US010647868B2

(12) United States Patent
Do et al.

(10) Patent No.: US 10,647,868 B2
(45) Date of Patent: May 12, 2020

(54) COATING PROVIDING MODULATED RELEASE OF VOLATILE COMPOSITIONS

(71) Applicant: ENVIROSCENT, INC., Atlanta, GA (US)

(72) Inventors: Bao Trong Do, Decatur, GA (US); Eric Mehnert, Lawrenceville, GA (US); Nicholas D. McKay, Jr., Atlanta, GA (US); Candace Branch, Smyrna, GA (US); Jeffrey Sherwood, Ellijay, GA (US)

(73) Assignee: ENVIROSCENT, INC., Atlanta, GA (US)

( * ) Notice: Subject to any disclaimer, the term of this patent is extended or adjusted under 35 U.S.C. 154(b) by 228 days.

(21) Appl. No.: 15/636,936

(22) Filed: Jun. 29, 2017

(65) Prior Publication Data

US 2017/0296688 A1    Oct. 19, 2017

Related U.S. Application Data

(60) Division of application No. 14/866,297, filed on Sep. 25, 2015, now Pat. No. 9,694,097, which is a continuation of application No. 14/500,089, filed on Sep. 29, 2014, now Pat. No. 9,149,552.

(51) Int. Cl.
*C09D 103/02* (2006.01)
*A61L 9/12* (2006.01)

(52) U.S. Cl.
CPC .............. *C09D 103/02* (2013.01); *A61L 9/12* (2013.01); *Y10T 428/249954* (2015.04); *Y10T 428/249959* (2015.04); *Y10T 428/249962* (2015.04); *Y10T 428/249987* (2015.04)

(58) Field of Classification Search
None
See application file for complete search history.

(56) References Cited

U.S. PATENT DOCUMENTS

| 324,853 A | 8/1885 | Laurier |
|---|---|---|
| 855,984 A | 6/1907 | Russell |
| 934,502 A | 9/1909 | Canon |
| 1,777,820 A | 7/1930 | Anenberg |

(Continued)

FOREIGN PATENT DOCUMENTS

| CA | 166642 | 12/2016 |
|---|---|---|
| CA | 3014426 | 12/2016 |

(Continued)

OTHER PUBLICATIONS

U.S. Appl. No. 15/179,832, "Non Final Office Action", dated May 2, 2018, 9 pages.

(Continued)

*Primary Examiner* — Michael P. Rodriguez
(74) *Attorney, Agent, or Firm* — Kilpatrick Townsend & Stockton LLP

(57) ABSTRACT

Described are modulating coatings that are configured to provide an improved release profile of a volatile composition from a base material, wherein the modulating coating includes a barrier substance that is configured to hinder a release of the volatile composition through the modulating coating, and a hygroscopic substance that is configured to facilitate the release of the volatile composition through the modulating coating.

19 Claims, 12 Drawing Sheets

(56) References Cited

U.S. PATENT DOCUMENTS

| | | |
|---|---|---|
| 1,878,401 A | 9/1932 | John |
| 1,988,141 A | 1/1935 | Schaller |
| 2,120,204 A | 6/1938 | Langhorst |
| 2,303,073 A | 11/1942 | Brown |
| 2,615,754 A | 10/1952 | Lindenberg |
| 2,626,833 A | 1/1953 | Valentine |
| 2,800,457 A | 7/1957 | Green et al. |
| 3,041,288 A | 6/1962 | Anthony |
| 3,415,758 A | 12/1968 | Powell et al. |
| 3,516,941 A | 6/1970 | Matson |
| 3,575,345 A | 4/1971 | Buck, Jr. |
| 3,634,564 A | 1/1972 | Okamoto et al. |
| 3,770,856 A | 11/1973 | Ueki et al. |
| 3,790,081 A | 2/1974 | Thornton et al. |
| 3,870,542 A | 3/1975 | Ida et al. |
| 3,954,928 A | 5/1976 | Imoto et al. |
| 4,020,156 A | 4/1977 | Murray et al. |
| 4,081,384 A | 3/1978 | Pracht |
| 4,210,487 A | 7/1980 | Driscoll |
| 4,234,627 A | 11/1980 | Schilling |
| 4,384,589 A | 5/1983 | Morris |
| 4,753,389 A | 6/1988 | Davis |
| 4,802,626 A | 2/1989 | Forbes et al. |
| 5,103,654 A | 4/1992 | Gee et al. |
| 5,112,688 A | 5/1992 | Michael |
| 5,145,842 A | 9/1992 | Driedger et al. |
| 5,233,680 A | 8/1993 | Fussell |
| 5,372,303 A | 12/1994 | Paul |
| 5,395,047 A | 3/1995 | Pendergrass, Jr. |
| 5,437,410 A | 8/1995 | Babasade |
| 5,503,332 A | 4/1996 | Glenn |
| 5,544,812 A | 8/1996 | Torres |
| 5,578,563 A | 11/1996 | Trinh et al. |
| 5,710,406 A | 1/1998 | Garris et al. |
| 5,763,038 A | 6/1998 | Wood |
| 5,763,788 A | 6/1998 | Friedhoff et al. |
| 5,771,503 A | 6/1998 | Valimaa et al. |
| 5,832,648 A | 11/1998 | Malone |
| 5,940,921 A | 8/1999 | Wood et al. |
| 6,014,788 A | 1/2000 | Jaffri |
| 6,039,488 A | 3/2000 | Krawczyk et al. |
| 6,158,668 A | 12/2000 | Burgeson et al. |
| 6,168,088 B1 | 1/2001 | Mobley |
| 6,183,596 B1 | 2/2001 | Matsuda et al. |
| 6,194,375 B1 | 2/2001 | Ness et al. |
| D438,606 S | 3/2001 | Jackson |
| D439,318 S | 3/2001 | Jackson |
| D439,644 S | 3/2001 | Jackson |
| 6,214,163 B1 | 4/2001 | Matsuda et al. |
| 6,248,703 B1 | 6/2001 | Finucane et al. |
| 6,261,483 B1 | 7/2001 | Frank et al. |
| 6,329,057 B1 | 12/2001 | Dungworth et al. |
| 6,575,383 B2 | 6/2003 | Dobler et al. |
| 6,668,482 B1 | 12/2003 | Ruffin et al. |
| 6,688,551 B1 | 2/2004 | He et al. |
| 6,803,033 B2 | 10/2004 | McGee et al. |
| 6,921,024 B2 | 7/2005 | Donnelly et al. |
| 6,954,963 B2 | 10/2005 | McKay |
| 7,177,846 B2 | 2/2007 | Moenickheim et al. |
| 7,235,261 B2 | 6/2007 | Smith et al. |
| 7,383,227 B2 | 6/2008 | Spooner et al. |
| D605,747 S | 12/2009 | Butler et al. |
| 7,664,705 B2 | 2/2010 | Walker et al. |
| 7,741,266 B2 | 6/2010 | Bell et al. |
| 7,945,511 B2 | 5/2011 | O'brien et al. |
| D693,449 S | 11/2013 | Wolf |
| D711,525 S | 8/2014 | Sanders et al. |
| 8,919,662 B2 | 12/2014 | Sherwood |
| D721,168 S | 1/2015 | Wolf |
| 9,132,204 B2 | 9/2015 | Mckay et al. |
| 9,149,552 B1 | 10/2015 | Do et al. |
| 9,381,266 B2 | 7/2016 | Sherwood |
| 9,694,096 B2 | 7/2017 | McKay et al. |
| 9,694,097 B2 | 7/2017 | Do et al. |
| D800,286 S | 10/2017 | Mckay et al. |
| 10,286,098 B2 | 5/2019 | Sherwood |
| 2002/0002536 A1 | 1/2002 | Braco |
| 2002/0052852 A1 | 5/2002 | Bozeman |
| 2002/0136886 A1 | 9/2002 | He et al. |
| 2002/0138351 A1 | 9/2002 | Houvener et al. |
| 2003/0024997 A1 | 2/2003 | Welch et al. |
| 2003/0055783 A1 | 3/2003 | Cataline et al. |
| 2003/0211799 A1 | 11/2003 | Yao et al. |
| 2003/0217003 A1 | 11/2003 | Weinflash et al. |
| 2004/0001891 A1 | 1/2004 | Smith et al. |
| 2004/0197221 A1 | 10/2004 | Stanley, III |
| 2004/0236688 A1 | 11/2004 | Bozeman |
| 2005/0125360 A1 | 6/2005 | Tidwell et al. |
| 2005/0204493 A1 | 9/2005 | Legus et al. |
| 2006/0147353 A1 | 7/2006 | Wang |
| 2006/0178954 A1 | 8/2006 | Thukral et al. |
| 2006/0221614 A1 | 10/2006 | Van Dyn Hoven |
| 2007/0057086 A1 | 3/2007 | Van Kippersluis |
| 2007/0187524 A1 | 8/2007 | Sherwood |
| 2007/0224232 A1 | 9/2007 | Sherwood |
| 2008/0008860 A1 | 1/2008 | Murray et al. |
| 2008/0009616 A1 | 1/2008 | Frank et al. |
| 2008/0017667 A1 | 1/2008 | Valinotti et al. |
| 2008/0286143 A1 | 11/2008 | Grodsky |
| 2008/0308648 A1 | 12/2008 | Pesu |
| 2011/0148329 A1 | 6/2011 | Demarest et al. |
| 2011/0198409 A1 | 8/2011 | Gorman |
| 2011/0256364 A1 | 10/2011 | Boyer et al. |
| 2011/0262377 A1* | 10/2011 | McKay .............. A01N 25/34 424/76.4 |
| 2011/0263477 A1 | 10/2011 | Scarabaggio et al. |
| 2015/0108242 A1 | 4/2015 | Sherwood |
| 2015/0136872 A1 | 5/2015 | Sherwood |
| 2015/0374869 A1 | 12/2015 | Mckay et al. |
| 2016/0089468 A1 | 3/2016 | Do et al. |
| 2016/0136317 A9 | 5/2016 | Sherwood |
| 2016/0136318 A9 | 5/2016 | Sherwood |
| 2016/0279276 A1 | 9/2016 | Sherwood |
| 2016/0279277 A1 | 9/2016 | Sherwood |
| 2017/0266333 A1 | 9/2017 | Mckay et al. |
| 2018/0133354 A1 | 5/2018 | Mehnert et al. |

FOREIGN PATENT DOCUMENTS

| | | |
|---|---|---|
| CA | 3009663 | 7/2017 |
| CN | 102917878 | 2/2013 |
| CN | 102917878 | 1/2016 |
| CN | ZL201630033464.2 | 11/2016 |
| DE | 20110608 | 3/2002 |
| EM | 002963934-0001 | 1/2016 |
| EM | 002963934-0002 | 1/2016 |
| EM | 002963934-0003 | 1/2016 |
| EM | 002963934-0004 | 1/2016 |
| EM | 002963934-0005 | 1/2016 |
| EP | 462605 | 12/1991 |
| EP | 1190725 | 3/2002 |
| EP | 1627647 | 2/2006 |
| EP | 2552499 A1 | 2/2013 |
| EP | 2552499 A4 | 6/2016 |
| EP | 3201279 | 8/2017 |
| EP | 3307333 | 4/2018 |
| GB | 914421 | 1/1963 |
| GB | 1221488 | 2/1971 |
| GB | 1226448 | 3/1971 |
| GB | 1387265 | 3/1975 |
| HK | 1184082 | 1/2014 |
| JP | 49072551 | 6/1974 |
| JP | 53159844 | 12/1978 |
| JP | 59154255 | 10/1984 |
| JP | 06284845 | 10/1994 |
| JP | 08289925 | 11/1996 |
| JP | 2000093495 | 4/2000 |
| JP | 2000107274 | 4/2000 |
| JP | 2000312712 | 11/2000 |
| JP | 2001224675 | 8/2001 |
| JP | 2006333904 | 12/2006 |
| JP | 2007051398 | 3/2007 |
| JP | 2008127360 | 6/2008 |
| JP | 2011057570 | 3/2011 |

(56) References Cited

FOREIGN PATENT DOCUMENTS

| | | |
|---|---|---|
| JP | D1431480 | 1/2012 |
| JP | 2013526906 | 6/2013 |
| JP | 1573788 | 3/2017 |
| KR | 2019940001095 | 2/1994 |
| KR | 1020070079756 | 8/2007 |
| KR | 1020100094762 | 8/2010 |
| KR | 300645686 | 6/2012 |
| KR | 1020130100049 | 9/2013 |
| KR | 30916010 | 7/2017 |
| KR | 30938308 | 12/2017 |
| KR | 101856793 | 5/2018 |
| WO | 9112029 | 8/1991 |
| WO | 9807405 | 2/1998 |
| WO | 9842818 | 10/1998 |
| WO | 9844294 | 10/1998 |
| WO | 9847477 | 10/1998 |
| WO | 9847478 | 10/1998 |
| WO | 9943667 | 9/1999 |
| WO | 02089862 | 11/2002 |
| WO | 2004020566 | 3/2004 |
| WO | 2006002395 | 1/2006 |
| WO | 2007016705 | 2/2007 |
| WO | 2006002395 | 8/2007 |
| WO | 2009078038 | 6/2009 |
| WO | 2011123723 | 10/2011 |
| WO | 2011129896 | 10/2011 |
| WO | 2013064501 | 5/2013 |
| WO | 2014025720 | 2/2014 |
| WO | 2014181015 | 11/2014 |
| WO | 2016053802 | 4/2016 |
| WO | 2016201089 | 12/2016 |
| WO | 2017124047 | 7/2017 |

OTHER PUBLICATIONS

U.S. Appl. No. 10/773,642, "Advisory Action", dated Jul. 31, 2015, 3 pages.
U.S. Appl. No. 10/773,642, "Final Office Action", dated Mar. 12, 2015, 26 pages.
U.S. Appl. No. 10/773,642, "Final Office Action", dated Jan. 30, 2017, 34 pages.
U.S. Appl. No. 10/773,642, "Non Final Office Action", dated Sep. 12, 2013, 22 pages.
U.S. Appl. No. 10/773,642, "Non-final office action", dated Dec. 20, 2013, 20 pages.
U.S. Appl. No. 10/773,642, "Non-Final Office Action", dated Jul. 15, 2016, 26 pages.
U.S. Appl. No. 10/773,642, "Non-Final Office Action", dated Jul. 17, 2014, 30 pages.
U.S. Appl. No. 11/571,240, "Final Office Action", dated Feb. 4, 2013, 10 pages.
U.S. Appl. No. 11/571,240, "Final Office Action", dated Nov. 2, 2011, 11 pages.
U.S. Appl. No. 11/571,240, "Final Office Action", dated Mar. 23, 2010, 12 pages.
U.S. Appl. No. 11/571,240, "Final Office Action", dated Feb. 13, 2014, 7 pages.
U.S. Appl. No. 11/571,240, "Non-Final Office Action", dated Aug. 2, 2012, 10 pages.
U.S. Appl. No. 11/571,240, "Non-Final Office Action", dated Nov. 25, 2013, 8 pages.
U.S. Appl. No. 11/571,240, "Non-Final Office Action", dated Aug. 5, 2009, 9 pages.
U.S. Appl. No. 11/571,240, "Notice of Allowance", dated Sep. 4, 2014, 10 pages.
U.S. Appl. No. 13/077,971, "Final Office Action", dated Apr. 2, 2014, 15 pages.
U.S. Appl. No. 13/077,971, "Final Office Action", dated Jan. 2, 2015, 19 pages.
U.S. Appl. No. 13/077,971, "Non-Final Office Action", dated Jul. 3, 2013, 16 pages.
U.S. Appl. No. 13/077,971, "Non-Final Office Action", dated Jul. 18, 2014, 19 pages.
U.S. Appl. No. 13/077,971, "Notice of Allowance", dated May 8, 2015, 9 pages.
U.S. Appl. No. 13/077,971, "Restriction Requirement", dated Dec. 20, 2012, 8 pages.
U.S. Appl. No. 14/582,531, "Non-Final Office Action", dated Sep. 17, 2015, 7 pages.
U.S. Appl. No. 14/582,531, "Notice of Allowance", dated Apr. 11, 2016, 5 pages.
U.S. Appl. No. 14/582,609, "Final Office Action", dated Jan. 18, 2017, 9 pages.
U.S. Appl. No. 14/582,609, "Non-Final Office Action", dated May 25, 2016, 10 pages.
U.S. Appl. No. 14/582,609, "Restriction Requirement", dated Feb. 26, 2016, 7 pages.
U.S. Appl. No. 14/851,763, "Final Office Action", dated Jul. 19, 2016, 11 pages.
U.S. Appl. No. 14/851,763, "Non-Final Office Action", dated Dec. 15, 2016, 6 pages.
U.S. Appl. No. 14/851,763, "Non-Final Office Action", dated Dec. 17, 2015, 9 pages.
U.S. Appl. No. 14/851,763, "Notice of Allowance", dated Apr. 14, 2017, 8 pages.
U.S. Appl. No. 14/866,297, "Non-Final Office Action", dated Aug. 30, 2016, 7 pages.
U.S. Appl. No. 14/866,297, "Notice of Allowance", dated Mar. 1, 2017, 14 pages.
U.S. Appl. No. 14/866,297, "Restriction Requirement", dated Apr. 22, 2016, 8 pages.
U.S. Appl. No. 15/179,774, "Final Office Action", dated Mar. 14, 2017, 10 pages.
U.S. Appl. No. 15/179,774, "Non-Final Office Action", dated Nov. 16, 2016, 10 pages.
U.S. Appl. No. 15/179,774, "Restriction Requirement", dated Aug. 30, 2016, 5 pages.
U.S. Appl. No. 15/179,832, "Advisory Action", dated Jun. 9, 2017, 4 pages.
U.S. Appl. No. 15/179,832, "Final Office Action", dated Mar. 3, 2017, 14 pages.
U.S. Appl. No. 15/179,832, "Non-Final Office Action", dated Jul. 17, 2017, 12 pages.
U.S. Appl. No. 15/179,832, "Non-Final Office Action", dated Nov. 9, 2016, 14 pages.
U.S. Appl. No. 15/179,832, "Restriction Requirement", dated Aug. 31, 2016, 6 pages.
U.S. Appl. No. 15/179,832, "Final Office Action", dated Nov. 27, 2017, 11 pages.
U.S. Appl. No. 29/534,919, "Restriction Requirement", dated Nov. 18, 2016, 5 pages.
CA 2,555,265, "Office Action", dated Jul. 17, 2012, 3 pages.
CA2,555,265, "Office Action", dated Mar. 5, 2014, 3 pages.
CN201630033464.2, "Notice to Undergo Registration Procedure and Notice to Grant Patent Right with English translation", dated Jul. 29, 2016, 5 pages.
CN201630033464.2, "Office Action with English translation", dated May 9, 2016, 4 pages.
EP11763485.7, "Extended European Search Report", dated May 18, 2016, 11 pages.
EP11763485.7, "Partial Supplementary European Search Report", dated Feb. 10, 2016, 6 pages.
KR10-2012-7028002, "Office Action", dated Jul. 20, 2017, 16 pages.
KR30-2016-0004728, "Office Action", dated Dec. 21, 2016, 4 pages.
PCT/US2015/052405, "International Preliminary Report on Patentability", dated Apr. 13, 2017, 8 pages.
PCT/US2016/036672, "International Search Report and Written Opinion", dated Oct. 18, 2016, 21 pages.
PCT/US2016/036672, "Invitation to Pay Add'l Fees and Partial Search Rpt", dated Aug. 23, 2016, 7 pages.
PCT/US2016/036672, "International Preliminary Report on Patentability", dated Dec. 21, 2017, 13 pages.

(56) References Cited

OTHER PUBLICATIONS

PCT/US2017/013593, "International Search Report and Written Opinion", dated May 18, 2017, 14 pages.
U.S. Appl. No. 62/279,323, "Provisional Patent Application filed Jan. 15, 2016 (unpublished)".
U.S. Appl. No. 15/179,832, Final Office Action dated Aug. 29, 2018, 9 pages.
U.S. Appl. No. 29/534,919, Non-Final Office Action dated Mar. 3, 2017, 8 pages.
U.S. Appl. No. 29/534,919, Notice of Allowance dated Jul. 14, 2017, 5 pages.
Canadian Application No. 166,642, Office Action dated May 25, 2016, 3 pages.
Japanese Application No. 2016-001725, Notice of Decision to Grant dated Feb. 9, 2017, (2 pages of English translation and 3 pages of original document).
Japanese Application No. 2016-001725, Office Action dated Nov. 1, 2016, (2 pages of English translation).
Korean Application No. 30-2017-3850, Office Action dated Jul. 31, 2017 (2 pages of English translation and 2 pages of original document).
Mexican Application No. MX/F/2016/000293, Office Action dated Apr. 14, 2016, (1 page of English translation and 2 pages of original document).
International Application No. PCT/US2017/013593, International Preliminary Report on Patentability dated Jul. 26, 2018, 9 pages.
U.S. Appl. No. 14/500,089, Non-Final Office Action, dated Feb. 12, 2015, 16 pages.
U.S. Appl. No. 14/500,089, Notice of Allowance, dated Jun. 5, 2015, 15 pages.
U.S. Appl. No. 14/851,763.
U.S. Appl. No. 14/866,297.
U.S. Appl. No. 29/534,919.
U.S. Appl. No. 60/582,670.
U.S. Appl. No. 61/319,431, filed Mar. 31, 2010.
U.S. Appl. No. 61/409,627, filed Nov. 3, 2010.
U.S. Appl. No. 61/419,959, filed Dec. 6, 2010.
U.S. Appl. No. 62/173,264.
Chinese Application No. 201180026620.7, Office Action, dated Feb. 12, 2014, 12 pages.
Chinese Application No. 201180026620.7, Office Action, dated Nov. 14, 2014, 15 pages.
Japanese Application No. 2013-502872, Office Action, dated Oct. 28, 2014, 11 pages.
Japanese Application No. 2013-502872, Office Action, with English translation, dated Jun. 30, 2015, 2 pages.
PCT Application No. PCT/US2005/022566, International Preliminary Report on Patentability, dated Jul. 10, 2007, 5 pages.
PCT Application No. PCT/US2005/022566, International Search Report and Written Opinion, dated Jun. 18, 2007, 6 pages.
PCT Application No. PCT/US2011/030842, International Preliminary Report on Patentability, dated Oct. 11, 2012, 7 pages.
PCT Application No. PCT/US2011/030842, International Search Report and Written Opinion, dated May 23, 2011, 8 pages.
PCT Application No. PCT/US2015/052405, International Search Report and Written Opinion, dated Dec. 4, 2015, 11 pages.
U.S. Appl. No. 62/279,374, filed Jan. 15, 2016.

* cited by examiner

COATING PROVIDING MODULATED RELEASE OF VOLATILE COMPOSITIONS

CROSS-REFERENCE TO RELATED APPLICATIONS

This application is a divisional of U.S. patent application Ser. No. 14/866,297, filed Sep. 25, 2015, which is a continuation of U.S. patent application Ser. No. 14/500,089, filed Sep. 29, 2014, now U.S. Pat. No. 9,149,552, issued Oct. 6, 2015, all of which are hereby incorporated in their entireties by this reference.

FIELD OF THE INVENTION

The field of the invention relates to articles that provide modulated release of volatile compositions, and more specifically relate to articles that provide a modulated release of volatile olfactory or fragrance compounds.

BACKGROUND

Fragrance-releasing devices are well known and commonly used in household and commercial establishments to provide a pleasant environment for people in the immediate space. Further, aroma-driven experiences are well recognized to improve or enhance the general mood of individuals. In some instances, fragrances may trigger memories of experiences associated with the specific scent. Whether it is providing a pleasant environment, affecting a general demeanor, or triggering a nostalgic memory, a steady, long-lasting release of fragrance will ensure consumer and customer satisfaction.

Fragrance-release devices based on passive diffusion are limited in their product-use by a finite supply of the fragrance and its evaporation rate from a surface. In some examples, the fragrance-release device is designed to carry the fragrance liquid within its architecture so that the fragrance supply is finite and determined by the size of the fragrance-release device.

The evaporation rate of fragrance from the fragrance-release device is determined, at least in part, by the composition of the fragrance, where compositions containing more volatile compounds (e.g. "top" notes) will evaporate faster than those with less volatile compounds (e.g. "base" notes). A fragrance composition determines its character. As a result, changing the composition of the fragrance will affect the character. The release rate profile of fragrance is generally strong (more intense) at the beginning of product use, followed by decreasing intensity over time. In some instances, the release rate exhibits a steep slope (as can be seen in the plot of fragrance release over time in FIG. 5 and the cumulative fragrance loss over time in FIG. 6), where the initial fragrance release is too strong and the fragrance release time is too short. For these fragrances, there is a need to modulate the release of fragrance from the fragrance-release device to provide a steady and long-lasting fragrance release without changing the fragrance load and character. Specifically there is a need to temper the release of fragrance compounds at the initial stage of product use, followed by facilitation of fragrance compound release at the later stage of product use.

SUMMARY

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings and each claim.

According to certain embodiments of the present invention, a modulating coating is configured to provide an improved release profile of a volatile composition from a base material, wherein the modulating coating comprises a barrier substance that is configured to hinder a release of the volatile composition through the modulating coating, and a hygroscopic substance that is configured to facilitate the release of the volatile composition through the modulating coating.

In some embodiments, the hygroscopic substance is configured to facilitate the release of the volatile composition through the modulating coating by attracting water molecules into the modulating coating to displace the volatile composition trapped by the barrier substance within the modulating coating.

In certain embodiments, the hygroscopic substance comprises silica. In these embodiments, the barrier substance may comprise maltodextrin.

According to some embodiments, the weight ratio of the barrier substance to the hygroscopic substance ranges from 99:1 to 1:99. The weight ratio of the barrier substance to the hygroscopic substance may further range from 25:75 to 75:25. The weight ratio of the barrier substance to the hygroscopic substance may also be approximately 50:50.

In certain embodiments, the particle size of the hygroscopic substance ranges from 0.001 µm-1 µm.

According to certain embodiments of the present invention, an article comprises a base material comprising an internal structure, a volatile composition, wherein at least some of the volatile composition is located in the internal structure, and a modulating coating at least partially located on at least one outer surface of the base material, wherein the modulating coating comprises a barrier substance and a hygroscopic substance.

In certain embodiments, the hygroscopic substance comprises silica. In these embodiments, the barrier substance may comprise maltodextrin.

According to some embodiments, the weight ratio of the barrier substance to the hygroscopic substance ranges from 99:1 to 1:99. The weight ratio of the barrier substance to the hygroscopic substance may further range from 25:75 to 75:25. The weight ratio of the barrier substance to the hygroscopic substance may also be approximately 50:50.

In certain embodiments, the particle size of the hygroscopic substance ranges from 0.001 µm-1 µm.

According to some embodiments, the base material may comprise a pulp composition.

In certain embodiments, at least some of the volatile composition is located within the modulating coating, wherein the modulating coating further comprises water that is absorbed or adsorbed to the hygroscopic substance.

According to certain embodiments of the present invention, an article comprises a base material comprising an internal structure comprising pores, a volatile composition, wherein at least some of the volatile composition is located in the pores, and a modulating coating at least partially located on at least one outer surface of the base material, wherein the article exhibits a ratio of a first day weight-loss value to a last day weight-loss value in a range of 1 to 20 over a 30 day life cycle of the article.

According to certain embodiments of the present invention, a method of coating a base material comprises applying a modulating coating to at least one outer surface of the base material, wherein the modulating coating comprises a barrier substance that hinders a release of a volatile composition through the modulating coating, and a hygroscopic substance that facilitates the release of the volatile composition through the modulating coating.

In certain embodiments, the modulating coating is applied to the at least one outer surface of the base material by at least one of gravure printing, offset printing, or flexographic printing. The modulating coating may also be applied to the at least one outer surface of the base material by at least one of a dip method, an infusion method, or spray treatment.

In certain embodiments, the method further comprises winding the base material into a spiral wound roll. The method may also further comprise converting the base material into an article having a three-dimensional structure.

BRIEF DESCRIPTION OF THE DRAWINGS

In the following detailed description, embodiments of the invention are described referring to the following figures.

DETAILED DESCRIPTION

Figure 1:
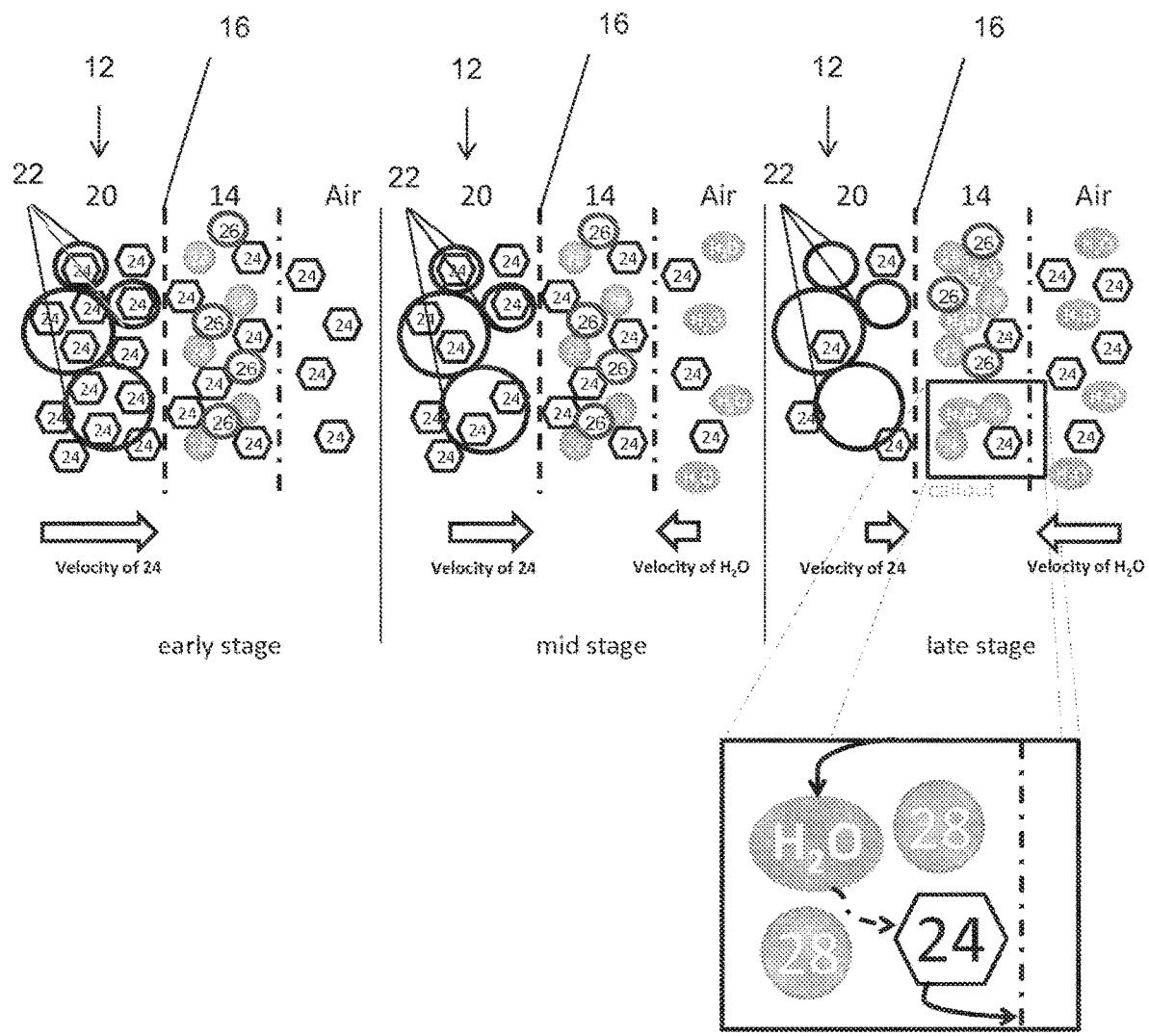
FIG. 1 is a schematic illustrating the movement of a volatile composition across an internal structure of a base material and a modulating coating over time, according to certain embodiments of the present invention.

The subject matter of embodiments of the present invention is described here with specificity to meet statutory requirements, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described.

According to certain embodiments of the present invention, an article 10 comprises a base material 12 and a modulating coating 14. The base material 12 may comprise an internal structure 20 comprising a plurality of pores 22 that are configured to provide locations for the volatile composition 24 to be stored therein and released therefrom, which is described in detail below.

As used herein, "coating" refers to any composition that can be applied using any suitable method to at least one of an outer surface of a three-dimensional article 10, to some or all surfaces of a base material 12, and/or may be uniformly or non-uniformly mixed throughout the internal structure 20 of the base material 12 and/or the article 10. In cases of surface application, the coating may be applied so that the composition may or may not penetrate to at least some degree within the article 10 and/or the base material 12.

The base material 12 may comprise natural and/or synthetic pulp compositions; pulp compositions combined with other products, including but not limited to paper, cellulose, cellulose acetate, pulp lap, cotton linters, biological plant-derived materials (from living plants), synthesized pulp compositions, and mixed pulps; polymer material; porous material; and/or extrudate.

As known in the art, pulp is primarily a collection of fibers with other components of the source material, wherein the fibers are derived from a natural or synthetic source material, for example, biological plants (natural) or petroleum-based synthesis products (synthetic). Pulp may be produced from various types of woods using any one of several known pulping techniques. The pulp may be from hardwoods, softwoods, or mixtures thereof. The pulp may also be made from recycled materials, and comprises recovering waste paper and remaking it into new products.

In certain embodiments, the number and/or size of the plurality of pores 22 (i.e., porosity) within the base material 12 may be controlled by the compactness and/or size of the fibers and/or particles that form the internal structure 20. For example, in certain embodiments of the base material 12 that comprise fibers, voids between the fibers form tiny air passages throughout the internal structure 20. The compactness of the fibers affects the degree in which the base material 12 allows gas or liquid to pass through it. For example, porosity may affect uptake or load amount of volatile compositions, or may affect the rate of release of such substances. Porosity of the base material 12 may be affected by adding other materials, such as additives to the matrix material 12 as it is being formed from a composition, such as pulp or any other composition described above, so that the additives are located within the internal structure 20 of the base material 12 after formation.

The porosity of a base material 12 that comprises pulp may be affected at any stage of the pulp production process. An increased level of fiber refining causes the fibers to bond together more strongly and tightly, making the pulp material denser, thereby reducing the network of air passages and the porosity. Surface sizing, coating, calendering or supercalendering may also seal and/or further compress surface fibers.

The porosity of the base material 12 is measured quantitatively as either the length of time it takes for a quantity of air to pass through a sample, or the rate of the passage of air through a sample, using either a Gurley densometer (in the first case) or a Sheffield porosimeter (in the second case). With the Gurley densometer, the porosity is measured as the number of seconds required for 100 cubic centimeters of air to pass through 1.0 square inch of a given material at a pressure differential of 4.88 inches of water, as described in ISO 5646-5, TAPPI T-460, or TAPPI T-536.

The porosity may affect how completely and how quickly the volatile composition 24 is absorbed into a pulp base material 12, as such absorption may occur primarily by capillary action. For example, a pulp base material 12 with high porosity may have increased absorbency of the volatile composition 24. The porosity of the pulp base material 12 may range from 0.01 Gurley second-100 Gurley seconds, and all ranges therein. In certain embodiments where there are multiple layers of pulp base material 12, the porosity may range from 0.01 Gurley second-20 Gurley seconds. The volatile composition 24 may be applied to the base material 12 in the form of a film, or a coating, or a treatment integrated into the internal structure 20 of the base material 12.

The volatile composition 24 may include but is not limited to fragrances, flavor compounds, odor-eliminating compounds, aromatherapy compounds, natural oils, water-based scents, odor neutralizing compounds, and outdoor products (e.g., insect repellent).

As used herein, "volatile substance" refers to any compound, mixture, or suspension of compounds that are odorous, or compound, mixture, or suspension of compounds that cancel or neutralize odorous compounds, such as any compound or combination of compounds that would produce a positive or negative olfactory sense response in a living being that is capable of responding to olfactory compounds, or that reduces or eliminates such olfactory responses.

A volatile composition as used herein comprises one or more volatile substances and is generally a composition that has a smell or odor, which may be volatile, which may be transported to the olfactory system of a human or animal, and is generally provided in a sufficiently high concentration so that it will interact with one or more olfactory receptors.

A fragrance may comprise an aroma or odorous compound, mixture or suspension of compounds that is capable of producing an olfactory response in a living being capable of responding to olfactory compounds, and may be referred to herein as odorant, aroma, or fragrance. A fragrance composition may include one or more than one of the fragrance characteristics, including top notes, mid notes or heart, and the dry down or base notes. The volatile composition 24 may comprise other diluents or additives, such as solvents or preservatives.

Examples of volatile compositions 24 useful in the present invention include but are not limited to, esters, terpenes, cyclic terpenes, phenolics which are also referred to as aromatics, amines and alcohols. For example, furaneol 1-hexanol, cis-3-Hexen-1-ol, menthol, acetaldehyde, hexanal, cis-3-hexenal, furfural, fructone, hexyl acetate, ethyl methylphenylglycidate, dihydrojasmone, wine lactone, oct-1-en-3-one, 2-Acetyl-1-pyrroline, 6-acetyl-2,3,4,5-tetrahydropyridine, gamma-decalactone, gamma-nonalactone, delta-octalactone, jasmine, massoia lactone, sotolon ethanethiol, grapefruit mercaptan, methanethiol, 2-methyl-2-propanethiol, methylphosphine, dimethylphosphine, methyl formate, nerolin tetrahydrothiophene, 2,4,6-trichloroanisole, substituted pyrazines, methyl acetate, methyl butyrate, methyl butanoate, ethyl acetate, ethyl butyrate, ethyl butanoate, isoamyl acetate, pentyl butyrate, pentyl butanoate, pentyl pentanoate, isoamyl acetate, octyl acetate, myrcene, geraniol, nerol, citral, lemonal, geranial, neral, citronellal, citronellol, linalool, nerolidol, limonene, camphor, terpineol, alpha-ionone, terpineol, thujone, benzaldehyde, eugenol, cinnamaldehyde, ethyl maltol, vanillin, anisole, anethole, estragole, thymoltrimethylamine, putrescine, diaminobutane, cadaverine, pyridine, indole and skatole. Most of these are organic compounds and are readily soluble in organic solvents, such as alcohols or oils. Fragrance includes pure fragrances such as those including essential oils and are known to those skilled in the art. Water-based odorous compounds and other odorous compositions are also contemplated by the present invention.

Fragrance oils as olfactory-active compounds or compositions usually comprise many different perfume raw materials. Each perfume raw material used differs from another by several important properties including individual character and volatility. By bearing in mind these different properties, and others, the perfume raw material can be blended to develop a fragrance oil with an overall specific character profile. To date, characters are designed to alter and develop with time as the different perfume raw materials evaporate from the substrate and are detected by the user. For example, perfume raw materials which have a high volatility and low substantivity are commonly used to give an initial burst of characters such as light, fresh, fruity, citrus, green or delicate floral to the fragrance oil which are detected soon after application. Such materials are commonly referred to in the field of fragrances as "top notes." By way of a contrast, the less volatile, and more substantive, perfume raw materials are typically used to give characters such as musk, sweet, balsamic, spicy, woody or heavy floral to the fragrance oil which, although may also be detected soon after application, also last far longer. These materials are commonly referred to as "middle notes" or "base notes." Highly skilled perfumers are usually employed to carefully blend perfume raw materials so that the resultant fragrance oils have the desired overall fragrance character profile. The desired overall character is dependent both upon the type of composition in which the fragrance oil will finally be used and also the consumer preference for a fragrance.

In addition to the volatility, another important characteristic of a perfume raw material is its olfactory detection level, otherwise known as the odor detection threshold (ODT). If a perfume raw material has a low odor detection threshold, only very low levels are required in the gas phase, or air, for it to be detected by the human, sometimes as low as a few parts per billion. Conversely, if a perfume raw material has a high ODT, larger amounts or higher concentrations in the air of that material are required before it can be smelled by the user. The impact of a material is its function of its gas phase or air concentration and its ODT. Thus, volatile materials, capable of delivering large gas-phase concentrations, which also have low ODTs, are considered to be impactful. To date, when developing a fragrance oil, it has been important to balance the fragrance with both low and high volatility raw materials since the use of too many high volatility materials could lead to a short lived, overwhelming scent. As such the levels of high odor impact perfume raw materials within a fragrance oil have traditionally been restricted.

As used herein the term "fragrance oil" relates to a perfume raw material, or mixture of perfume raw materials, that are used to impart an overall pleasant odor profile to a composition, preferably a cosmetic composition. As used herein the term "perfume raw material" relates to any chemical compound which is odorous when in an unentrapped state, for example in the case of pro-perfumes, the perfume component is considered to be a perfume raw material, and the pro-chemistry anchor is considered to be the entrapment material. In addition "perfume raw materials" are defined by materials with a ClogP value preferably greater than about 0.1, more preferably greater than about 0.5, even more preferably greater than about 1.0. As used herein the term "ClogP" means the logarithm to base 10 of the octanol/water partition coefficient. This can be readily calculated from a program called "CLOGP," which is available from Daylight Chemical Information Systems Inc., Irvine Calif., USA. Octanol/water partition coefficients are described in more detail in U.S. Pat. No. 5,578,563.

Examples of residual "middle and base note" perfume raw materials include, but are not limited to, ethyl methyl phenyl glycidate, ethyl vanillin, heliotropin, indol, methyl anthranilate, vanillin, amyl salicylate, coumarin. Further examples of residual perfume raw materials include, but are not limited to, ambrox, bacdanol, benzyl salicylate, butyl anthranilate, cetalox, ebanol, cis-3-hexenyl salicylate, lilial, gamma undecalactone, gamma dodecalactone, gamma decalactone, calone, cymal, dihydro iso jasmonate, iso eugenol, lyral, methyl beta naphthyl ketone, beta naphthol methyl ether, para hydroxylphenyl butanone, 8-cyclohexadecen-1-one, oxocyclohexadecen-2-one/habanolide, florhydral, intreleven aldehyde.

Examples of volatile "top note" perfume raw materials include, but are not limited to, anethol, methyl heptine carbonate, ethyl aceto acetate, para cymene, nerol, decyl aldehyde, para cresol, methyl phenyl carbinyl acetate, ionone alpha, ionone beta, undecylenic aldehyde, undecyl aldehyde, 2,6-nonadienal, nonyl aldehyde, octyl aldehyde. Further examples of volatile perfume raw materials include, but are not limited to, phenyl acetaldehyde, anisic aldehyde, benzyl acetone, ethyl-2-methyl butyrate, damascenone, damascone alpha, damascone beta, flor acetate, frutene, fructone, herbavert, iso cyclo citral, methyl isobutenyl tetrahydro pyran, isopropyl quinoline, 2,6-nonadien-1-ol, 2-methoxy-3-(2-methylpropyl)-pyrazine, methyl octine carbonate, tridecene-2-nitrile, allyl amyl glycolate, cyclogalbanate, cyclal C, melonal, gamma nonalactone, c is 1,3-oxathiane-2-methyl-4-propyl.

Other useful residual "middle and base note" perfume raw materials include, but are not limited to, eugenol, amyl cinnamic aldehyde, hexyl cinnamic aldehyde, hexyl salicylate, methyl dihydro jasmonate, sandalore, veloutone, undecavertol, exaltolide/cyclopentadecanolide, zingerone, methyl cedrylone, sandela, dimethyl benzyl carbinyl butyrate, dimethyl benzyl carbinyl isobutyrate, triethyl citrate, cashmeran, phenoxy ethyl isobutyrate, iso eugenol acetate, helional, iso E super, ionone gamma methyl, pentalide, galaxolide, phenoxy ethyl propionate.

Other volatile "top note" perfume raw materials include, but are not limited to, benzaldehyde, benzyl acetate, camphor, carvone, borneol, bornyl acetate, decyl alcohol, eucalyptol, linalool, hexyl acetate, iso-amyl acetate, thymol, carvacrol, limonene, menthol, iso-amyl alcohol, phenyl ethyl alcohol, alpha pinene, alpha terpineol, citronellol, alpha thuj one, benzyl alcohol, beta gamma hexenol, dimethyl benzyl carbinol, phenyl ethyl dimethyl carbinol, adoxal, allyl cyclohexane propionate, beta pinene, citral, citronellyl acetate, citronellal nitrile, dihydro myrcenol, geraniol, geranyl acetate, geranyl nitrile, hydroquinone dimethyl ether, hydroxycitronellal, linalyl acetate, phenyl acetaldehyde dimethyl acetal, phenyl propyl alcohol, prenyl acetate, triplal, tetrahydrolinalool, verdox, cis-3-hexenyl acetate.

In certain embodiments, the volatile composition 24 may comprise a fragrance component having a release rate ranging from 0.001 g/day to 2.0 g/day. The formulation of the fragrance may comprise any suitable combination of top, mid, and base note components.

Figure 2:
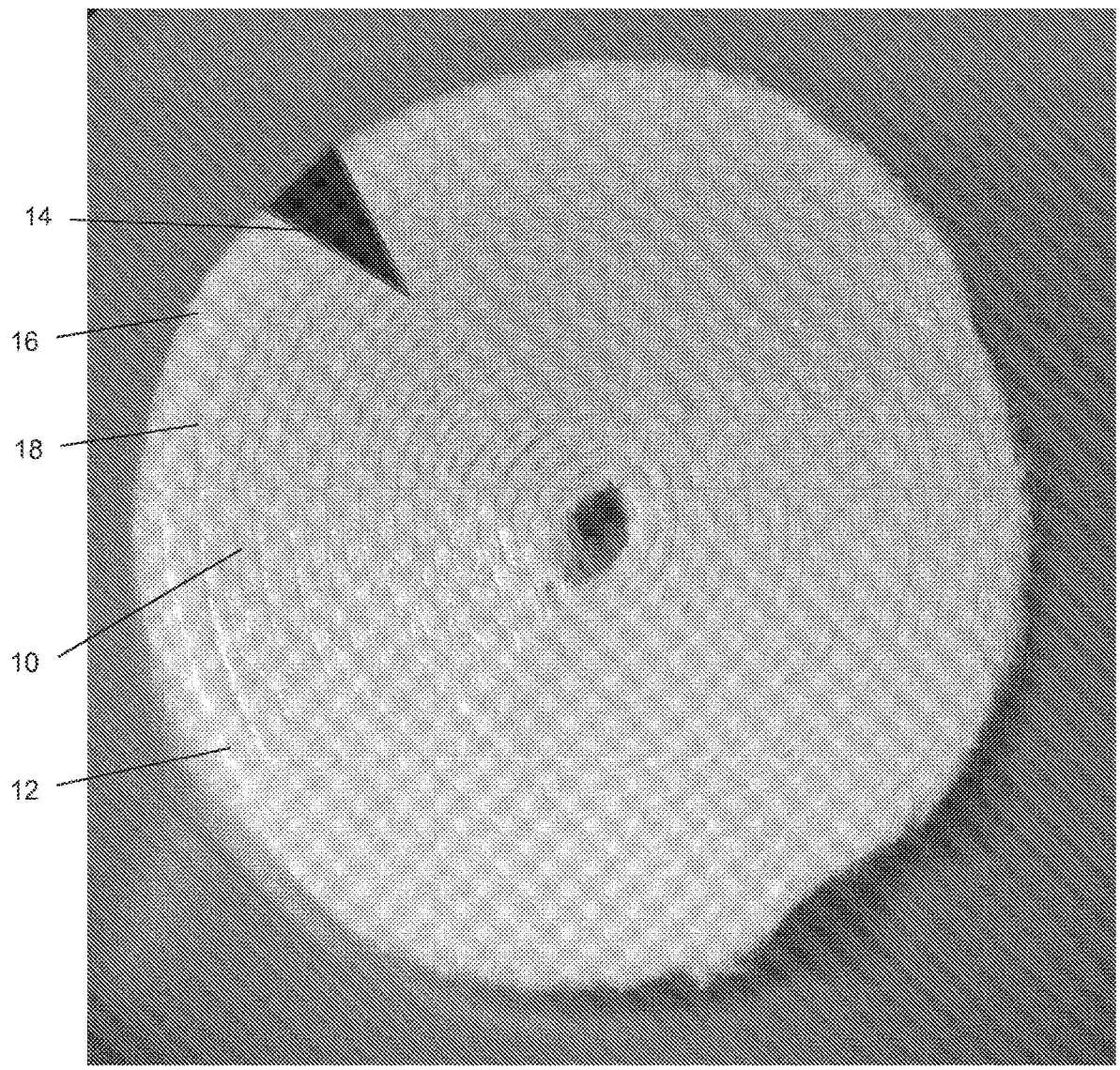
FIG. 2 is a cross-sectional view of an article formed from a base material and coated with a modulating coating, according to certain embodiments of the present invention. The triangle schematic represents a concentration gradient of modulating coating 14 based on depth of penetration.
Figure 3:
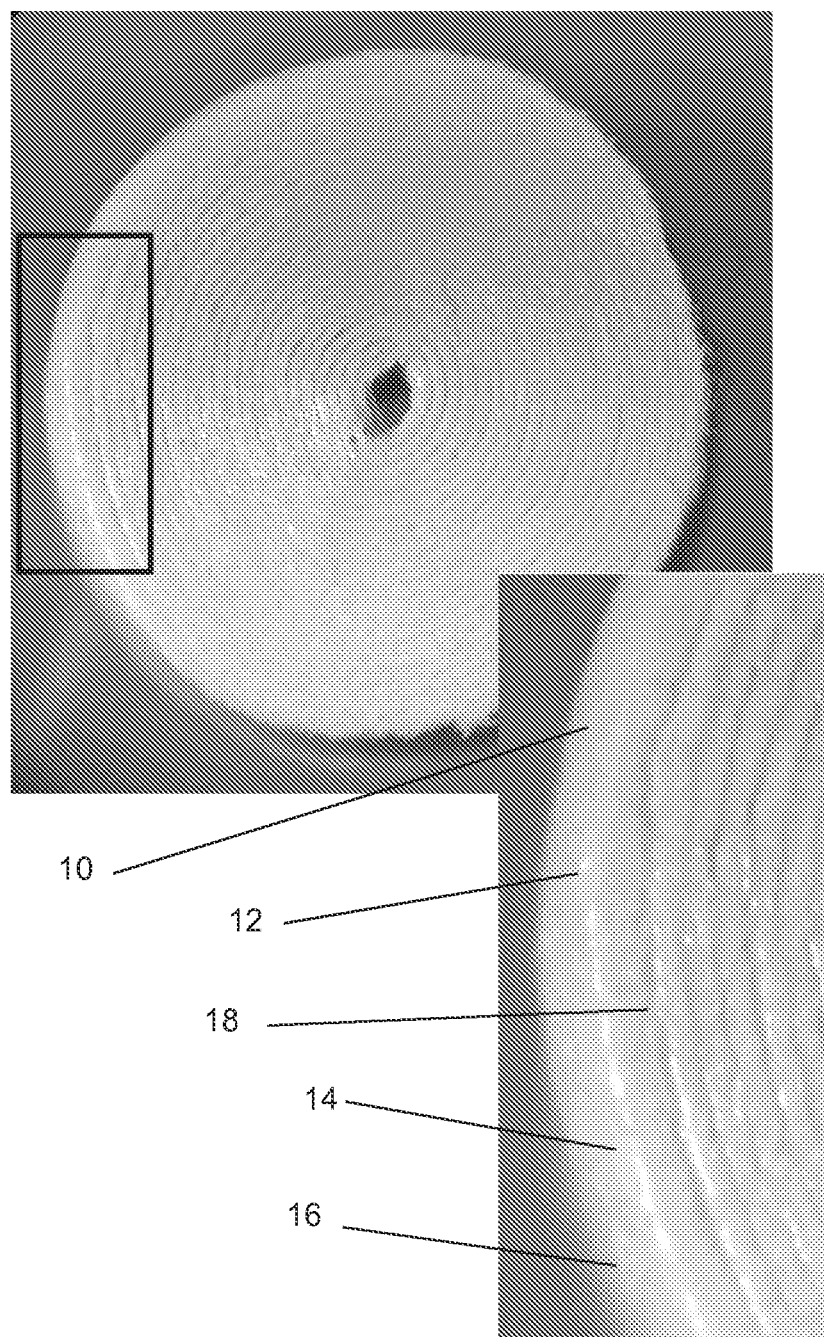
FIG. 3 is another cross-sectional view and a partial close-up view of the article of FIG. 2.
Figure 4:
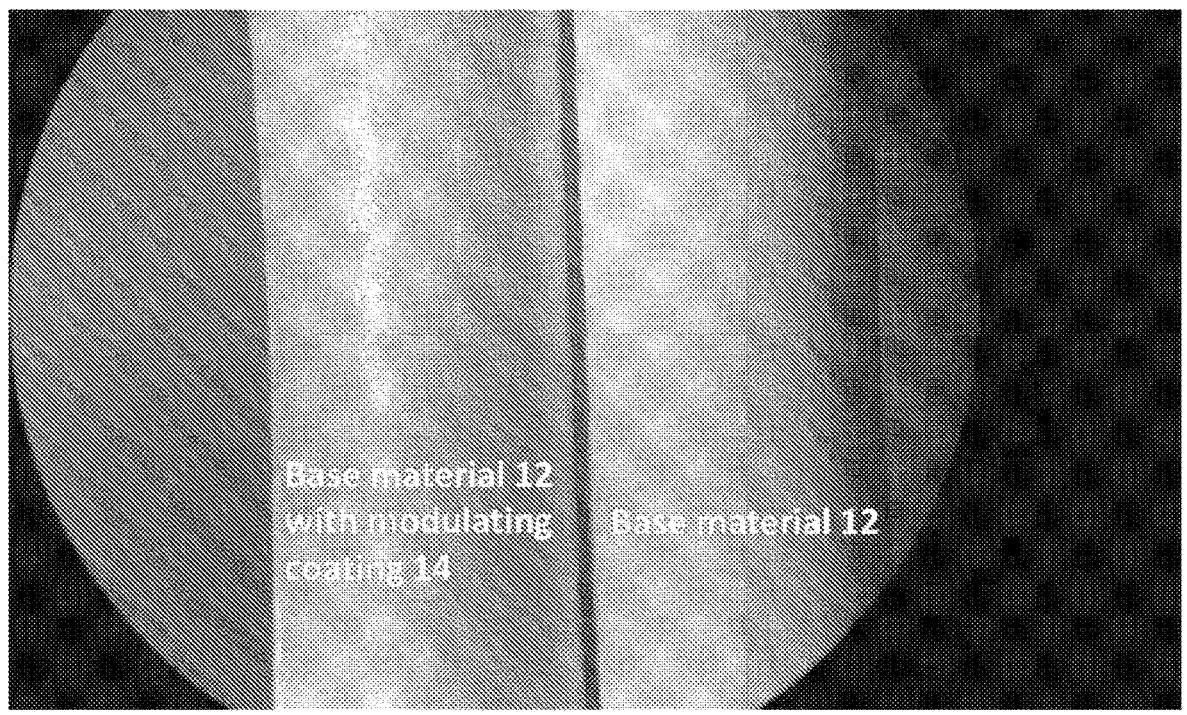
FIG. 4 is a view of an outer surface of articles formed from a base material with the article on the left coated with the modulating coating and the article on the right uncoated, according to certain embodiments of the present invention.
Figure 5:
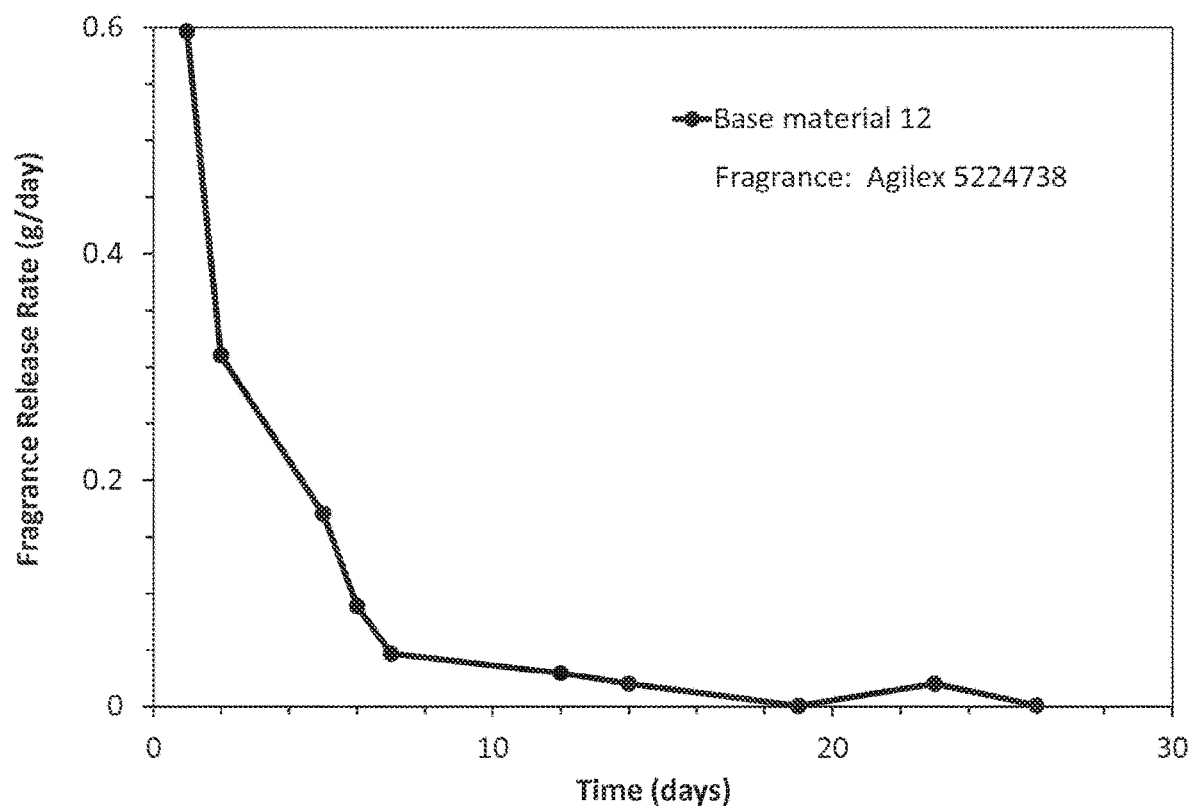
FIG. 5 is a graph showing the release rate in grams per day of a volatile composition loaded in an uncoated article.
Figure 6:
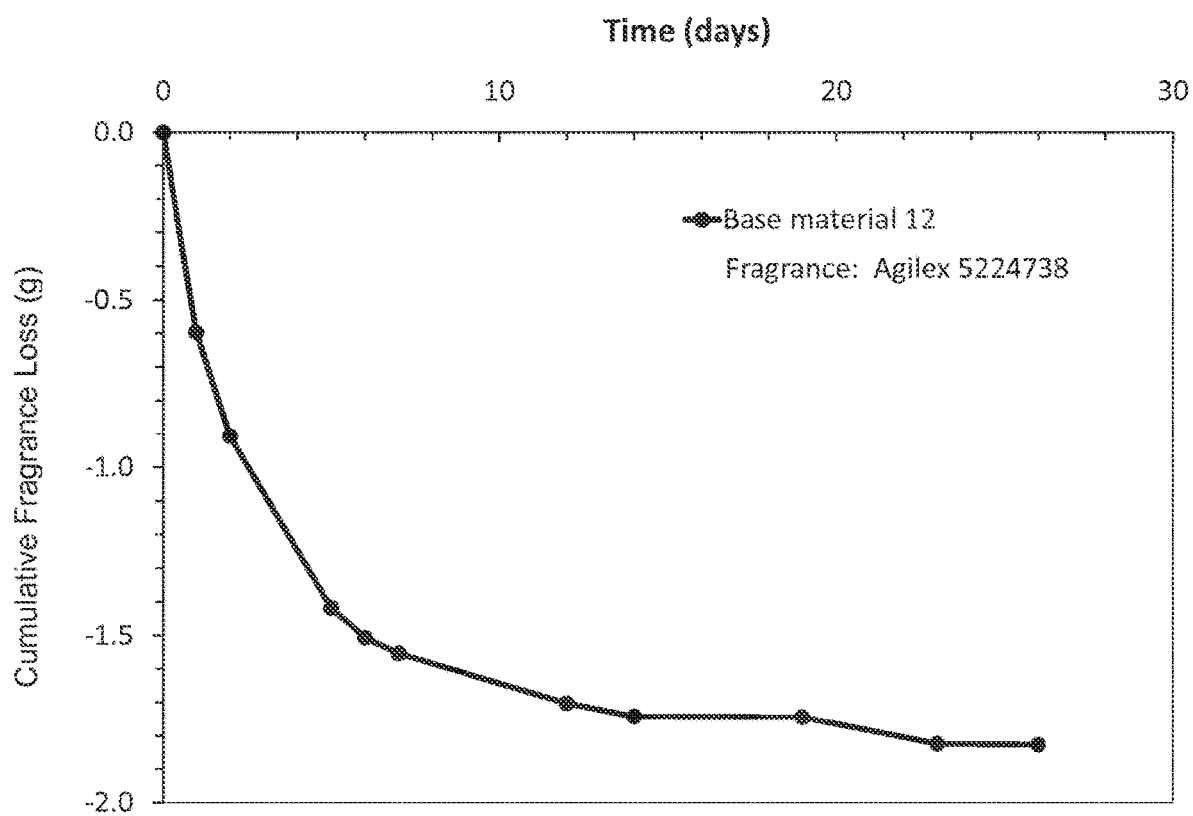
FIG. 6 is a graph showing the cumulative amount released over time of a volatile composition loaded in an uncoated article.

The modulating coating 14 may be applied to at least one outer surface 16 of the base material 12 and/or to the article 10, and may be applied before or after loading of the volatile composition 24. In certain embodiments, as best illustrated in FIGS. 2-3, the modulating coating 14 may penetrate into the internal structure 20 of the base material 12 to a certain level, which may vary depending on the porosity, processing methods, or other characteristics of the base material 12.

The modulating coating 14 is designed to slow the release rate of the volatile composition 24 loaded into the internal structure 20 at higher concentration levels and accelerate the release rate of the volatile composition 24 at lower concentration levels in order to achieve a relatively steady release of volatile composition 24 over time, as illustrated in FIGS. 7-8 and 11-12.

To explain the way that the modulating coating 14 works to have this "hold/push" effect over a range of load levels of the volatile composition 24, it is necessary to explain the way in which the release rate of the volatile composition 24 is generated. The volatile composition 24 is loaded or absorbed into the internal structure 20 via the pores 22 until a sufficiently high load level is achieved within the internal structure 20 through various embodiments of loading methods, which are explained in detail below. The volatile composition 24 may be loaded or absorbed into the internal structure 20 before or after the modulating coating 14 is applied.

The initially high load level of the volatile composition 24 within the internal structure 20 creates an internal force that causes the volatile composition 24 to diffuse or evaporate out of the internal structure 20 as quickly as possible to a region of lower concentration. As the load level of the volatile composition 24 decreases over time, the force that causes the diffusion or evaporation diminishes until there is no longer a force remaining (i.e., an equilibrium point is reached where the volatile composition 24 no longer diffuses or evaporates out of the internal structure 20). The equilibrium point is usually higher than 0% concentration, which causes some of the volatile composition 24 to become trapped within the pores 22 of the internal structure 20.

In conventional applications, such as in U.S. Publication No. 20110262377, a coating may be applied to form a layer that slows or retards the rapid release of a volatile composition at higher concentration levels. These conventional coatings typically include substances that trap some of the volatile composition within the coating layer, which slows down the rate of release through the coating. However, because the coating only serves as a barrier or "speed bump" to slow down the rate of release of the volatile composition, the release will eventually stop once the concentration of volatile composition within the internal structure reaches equilibrium (i.e., a level where there is no longer a sufficient concentration to drive the volatile composition through the coating layer, thus allowing some of volatile composition to remain trapped within the coating layer and/or within the internal structure).

The modulating coating 14 comprises both a barrier substance 26 and a hygroscopic substance 28. In particular, in most embodiments, the modulating coating 14 comprises substances that do not chemically interact with the volatile composition 24 itself.

In these embodiments, when the modulating coating 14 is applied to the outer surface 16 of the internal structure 20, at the higher concentration levels of the volatile composition 24 within the internal structure 20, the barrier substance 26 forms a barrier or "speed bump" to slow down the rate of release of the volatile composition 24 through the modulating coating 14. At these higher initial concentration levels, as illustrated in the early stage section of FIG. 1, the hygroscopic substance 28 does not play a role in modulating the release rate of the volatile composition 24 (i.e., does not absorb any water into the modulating coating 14) because the concentration of the volatile composition 24 within the internal structure 20 is sufficiently high to force a certain amount of the volatile composition 24 to release through the modulating coating 14 at a rate that effectively blocks any water from being attracted into the modulating coating 14 by the hygroscopic substance 28.

As the concentration level of the volatile composition 24 within the internal structure 20 slowly diminishes, as illustrated in the mid stage section of FIG. 1, the concentration of the volatile composition 24 within the internal structure 20 is still sufficiently high to continue to force some of the volatile composition 24 out of the modulating coating 14 at a reduced rate of release.

One hypothesis to explain the phenomenon observed in the late stage, as suggested in the graphs of release rate over time in FIGS. 7-8 and 11-12, is that because there is a lower volume of the volatile composition 24 exiting the modulating coating 14, the hygroscopic substance 28 begins to attract more water (typically in the form of water vapor) into the modulating coating 14, whereupon the water adsorbs or absorbs to the hygroscopic substance 28 and begins to displace the volatile composition 24 that is trapped by the barrier substance 26 within the modulating coating 14. This hypothesis is illustrated in the late stage section of FIG. 1, and is based on known physical properties of the hygroscopic substance 28 and the data showing higher release rates at the end of the product life cycle, as compared to the same product without the modulating coating 14. Once displaced, the volatile composition 24 is released from the modulating coating 14, thereby creating an aggregate rate of release of the volatile composition 24 that may approximate the rate of release driven by the higher load level of the volatile composition 24 alone.

As the load level of volatile composition 24 continues to drop to a level that can no longer drive the volatile composition 24 out of the modulating coating 14, the hygroscopic substance 28 continues to pull more and more water into the modulating coating 14. That water continues to displace the trapped volatile composition 24, effectively forcing the displaced volatile composition 24 to be released from the modulating coating 14. For a period of time in the late stage, as illustrated in FIGS. 7-8 and 11-12, the rate of release of the volatile composition 24 due to water displacement driven by the hygroscopic substance 28 may approximate the rate of release driven by the higher load level of the volatile composition 24 alone and/or may approximate the aggregate rate of release driven by both the higher load level of the volatile composition 24 and water displacement driven by the hygroscopic substance 28. As a result, where conventional coatings that contain only barrier substances 26 may have stopped releasing volatile compositions once the equilibrium point of the concentration is reached within the internal structure 20, the modulating coating 14 continues to provide a relatively constant release of the volatile composition 24.

An alternate hypothesis to explain the phenomenon observed in the late stage as seen in FIGS. 7-8 and 11-12 is that the water that is brought into the modulating coating 14 by the hygroscopic substance 28 may act to degrade the barrier substance 26, which would also allow for release of the volatile composition 24 trapped within the modulating coating 14 and within the internal structure 20 of the base material 12.

In any event, the test results demonstrate that the modulating coating 14 generates an improved release profile of the volatile composition 24 over the aromatic life cycle of the article 10, depending on the porosity of the internal structure 20 of the base material 12 and the volatility levels of the volatile composition 24. Eventually, the concentration of the volatile composition 24 within the internal structure 20 and the amount trapped by the barrier substances 26 within the modulating coating 14 will reach such a low point that the amount of volatile composition 24 released on a daily basis by the modulating coating 14 will eventually decline to zero.

In certain embodiments, the barrier substance 26 may comprise maltodextrin (e.g. Maltrin). In other embodiments, the barrier substance 26 may include but is not limited to other dextrins, other film-forming polysaccharides, other carbohydrates (mono-, di-, tri-, etc.), natural unmodified starch, modified starch, any starch appropriate for use in papermaking, as well as combinations of starch types, dextrin types, and combinations of starches and dextrins. In certain embodiments, the barrier substance 26 may include but not is limited to additives such as insolubilizers, lubricants, dispersants, defoamers, crosslinkers, binders, surfactants, leveling agents, wetting agents, surface additives, rheology modifiers, non-stick agents, and other coating additives.

In certain embodiments, the hygroscopic substance 28 may comprise silica (e.g. silica nanoparticles). In other embodiments, the hygroscopic substance 28 may include but is not limited to other hygroscopic reagents, activated charcoal, calcium sulfate, calcium chloride, and molecular sieves, or other suitable water absorbing materials.

The weight ratio of the barrier substance 26 to the hygroscopic substance 28 may range from 99:1 to 1:99, and all ranges therein between. In certain embodiments, weight ratio of the barrier substance 26 to the hygroscopic substance 28 may further range from 25:75 to 75:25. In yet other embodiments, the weight ratio of the barrier substance 26 to the hygroscopic substance 28 may be approximately 50:50.

In certain embodiments, the particle size of the hygroscopic substance 28 is determined in part by the amount of surface area needed to attract enough water to counteract the drop in release rate due to a reduction in the load level of the volatile composition 24. The hygroscopic substance 28 is also configured so that it will attract water vapor, rather than liquid water. As a result, the diameter of the particle size of the hygroscopic substance 28 may range from 0.001 μm-1 μm, and all ranges therein between, and may further range from 1 nm-100 nm, which will attract the appropriate amount of water vapor molecules, as well as providing a more even coating.

In certain embodiments, the hygroscopic substance 28 may have a surface charge range that ensures interaction with the barrier substances 26. For example, in the case of silica, the surface charge ranges from −10 mV to −4000 mV, as measured by Zeta potential, which is a highly anionic point charge. When the silica is mixed with the maltodextrin before coating, the maltodextrin may group around the silica particles, which may further assist with the barrier formation within the modulating coating 14.

In certain embodiments, the modulating coating 14 may provide a more consistent release rate of the volatile compound 24. The consistency (variance) may be measured by the following formula.

$$\text{Variance}_{(Weight\text{-}loss\ ratio)} = \text{First day weight-loss value} / \text{Last day weight-loss value}$$

The benefit of the modulating coating 14 is to reduce the variance within a ratio range of 1 to 20 over a life cycle of the article, which in certain embodiments may be 30 days, but could be longer or shorter as needed or desired. As exhibited in Example 6, FIG. 7, the reduction in Variance$_{(Weight\text{-}loss\ ratio)}$ for pulp base material 12 treated with modulating coating 14 (i.e., the ratio range) is approximately 10.

Figure 9:
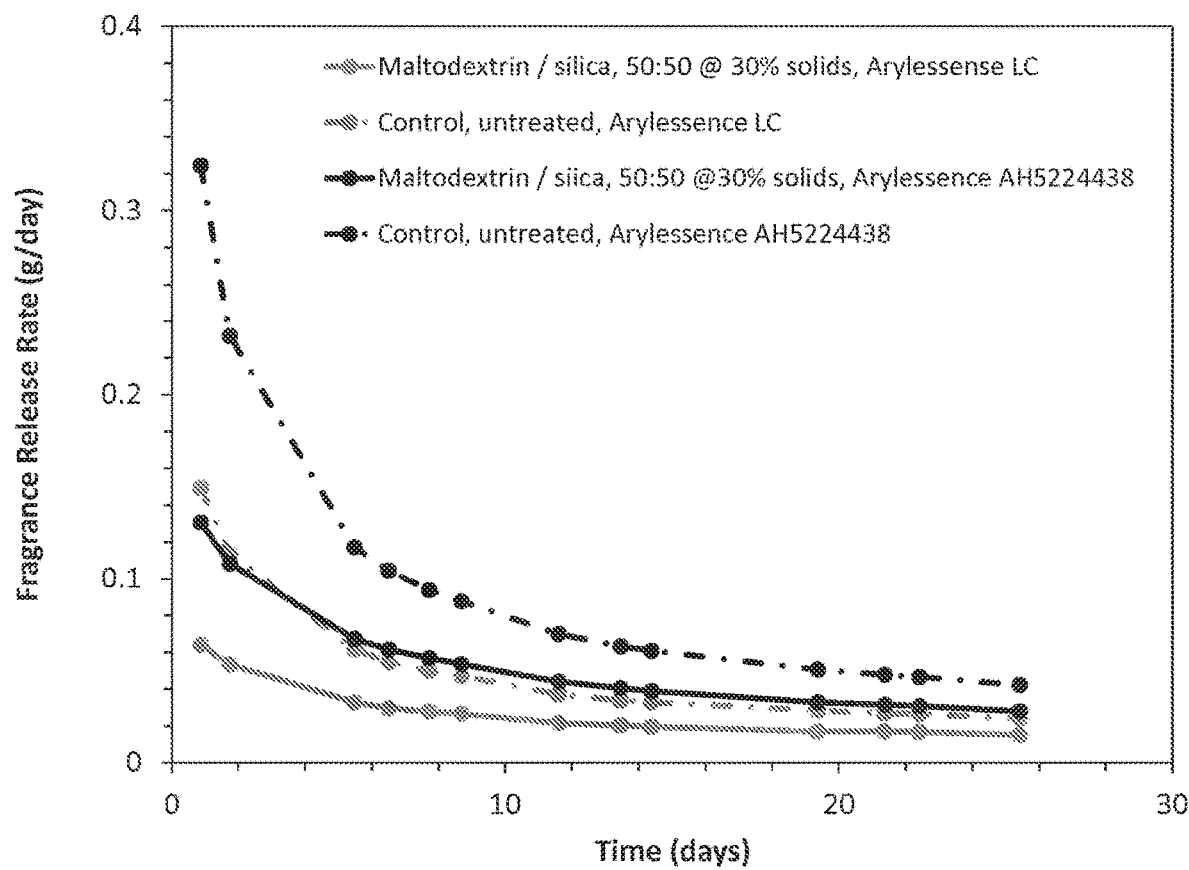
FIG. 9 is a graph showing the release rate in grams per day of a concentrated volatile composition loaded in an article coated with a modulating coating and loaded in an uncoated article, as well as the release rate in grams per day of a standard concentration of a volatile composition loaded in an article coated with a modulating coating and loaded in an uncoated article.
Figure 10:
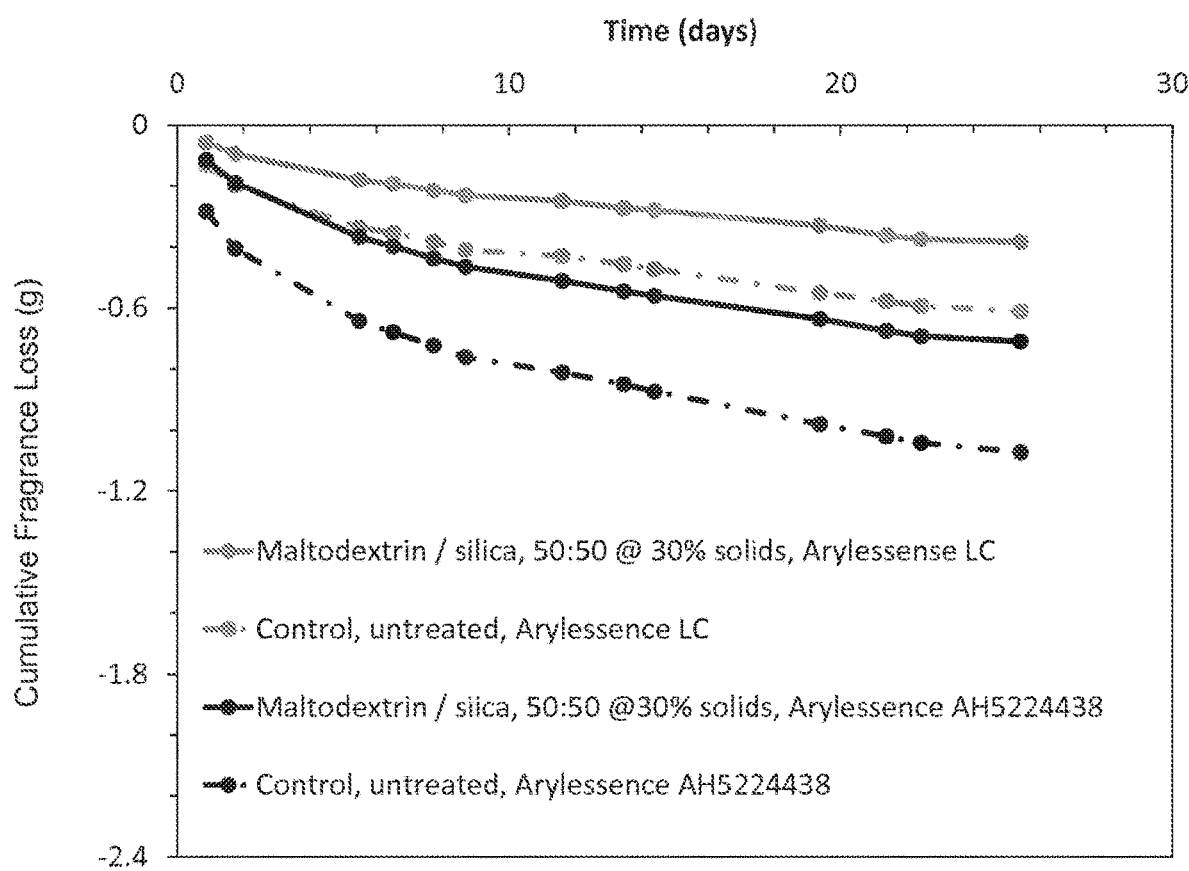
FIG. 10 is a graph showing the cumulative amount released over time of a concentrated volatile composition loaded in an article coated with a modulating coating and loaded in an uncoated article.

Furthermore, as demonstrated in Example 7 and accompanying FIGS. 9-10, in certain embodiments, use of a more concentrated version of the volatile composition 24 in combination with the modulating coating 14 provides release rate improvement as disclosed herein and presents commercial advantages over the use of the standard version of volatile composition 24 without modulating coating 14. The term "concentrated" used herein is intended to describe a higher amount of olfactory-active compounds or compositions relative to other non-volatile substances within the volatile composition 24. A more concentrated version of a volatile composition 24 will release into the atmosphere faster than its standard version, thus providing a higher than desired scent intensity and character. Application of modulating coating 14 will moderate this faster release, resulting in a new release rate that has the desired intensity and character.

In certain embodiments, the loaded amount of a more concentrated version of the volatile composition 24 into base material 12 coated with modulating coating 14 may be less than the loaded amount of the standard version of a volatile composition 24. This increased concentration, in combination with the optimal release rate, provides the opportunity for an increased duration of release and/or for material cost savings (by reducing the initial volatile composition load).

The base material 12 may be converted into the article 10, which may occur before or after the modulating coating 14 and/or the volatile composition 24 are applied.

In certain embodiments, the article 10 may comprise a single two-dimensional layer with varying shapes and thicknesses, such as flat sheet embodiments, wherein the modulating coating 14 may be applied to both the outer surface 16 and an opposing surface 18 of the base material 12.

In other embodiments, the article 10 may comprise multiple two-dimensional layers with varying shapes and thicknesses, wherein the modulating coating 14 may be applied to both the outer surface 16 of each layer of the base material 12 and arranged so that each uncoated opposing surface 18 is mated with an adjacent coated outer surface 16 of the next layer.

In further embodiments, the article 10 may comprise a three-dimensional structure with varying shapes and sizes, such as a desired shape, a solid rod, a rod with a core, a rod with two cores, a rod with a honeycomb structure, a solid sphere, a hollow sphere, or any other geometric shape, or other possible arrangements.

In certain embodiments, the article 10 may comprise a spiral wound paper. The spiral winding process allows for the paper to be the same or different for each layer formed by winding the paper one complete revolution around the axis of the structural component. For example, a structural component may comprise a rod shape, formed by winding the base material 12 (e.g., a paper matrix) around a vertical axis, so that a rod having a length longer than its diameter is formed. Each layer formed by the complete revolution of the paper matrix around the axis may be referred to as a ply. For example, a 10 ply rod may have from one to ten different characteristics for each ply of the rod. Characteristics may include but are not limited to absorbance, tensile strength density, pH, porosity, and polarity of the base material 12, and the type of paper or internal structure 20.

The modulating coating 14 may be applied to the base material 12 before or after application of the volatile composition 24. For example, the modulating coating 14 may be applied when the base material 12 is in a two-dimensional form via conventional two-dimensional coating methods typically used for treating two-dimensional sheets of material, such as paper. These methods include but are not limited to at least one of gravure printing, offset printing, flexographic printing, rod coating, blade coating, curtain coating, or other suitable coating methods. In these two-dimensional embodiments, the modulating coating 14 may be applied to the base material 12 when the base material 12 is in a single two-dimensional layer, after which the base material 12 layers are assembled together to form the article 10. In other two-dimensional embodiments, the base material 12 may be arranged into the layered material prior to application of the modulating coating 14 so that the modulating coating 14 is only applied to the outermost surface 16 of the top layer of the base material 12 (although the modulating coating 14 may penetrate to a certain depth within the article 10).

The modulating coating 14 may also be applied to the base material 12 after it has been formed into the three-dimensional article 10. In these embodiments, the modulating coating 14 may be applied to an outer surface of the article 10 (although the modulating coating 14 may penetrate to a certain depth within the article 10, as illustrated in FIGS. 2-3).

For example, the modulating coating 14 may be applied to the three-dimensional article 10 via a dip method where the three-dimensional article 10 is placed within a volume of modulating coating 14 for a specified amount of time, then removed and allowed to dry. The dip method may also be used with two-dimensional versions of the article 10. The add-on level may range from 0.1% to 10% by weight. Examples 2 and 3 describe specific non-limiting examples of dip treatment.

In other embodiments, the modulating coating 14 may be applied to the three-dimensional article 10 via an infusion method with the add-on infusion ranging from 1% to 20% by weight, and, in certain embodiments, may further range from 10% to 20% by weight. The infusion method may also be used with two-dimensional versions of the article 10. Example 4 describes a specific non-limiting example of infusion treatment.

In yet other embodiments, the modulating coating 14 may be applied to two-dimensional base material 12, two-dimensional articles 10 and/or three-dimensional articles 10 via spray treatment.

The volatile composition 24 may be applied to the base material 12 before or after application of the modulating coating 14, as described above. For example, the volatile composition 24 may be applied by placing the base material 12 and/or the article 10 in intimate contact with the volatile composition 24 for a period of time. The volatile composition 24 may be in any physical state, such as liquid, solid, gel, or gas. For convenience, a liquid volatile composition 24 is described, but this is not intended to be limiting. The interaction time may depend on the concentration or type of volatile composition 24 being applied to the base material 12 and/or the article 10, and/or how strong or intense of a volatile composition 24 release desired, and/or the type of base material 12. In certain embodiments, a rolled paper rod structural component with dimensions of 13.97 cm (length) and 0.64 cm (diameter) may be saturated with a liquid fragrance composition comprising approximately one (1) to three (3) grams of one or more pure fragrances, and the saturation time (interaction time) may range from less than one minute to a several hours, to several days. The base material 12 and/or the article 10 may be pre-treated prior to exposure to the volatile composition 24. For example, the base material 12 and/or the article 10 may be placed in a drying oven to remove any residual moisture. Further method steps comprise pressure treating and/or vacuum treating the base material 12 and/or the article 10. After treatment, the base material 12 and/or the article 10 may be dried, for example by rubbing or patting dry, and/or by other methods known for drying a surface, and/or may be left to air dry. Drying steps may be used before or after other steps described herein.

In some embodiments, a method for applying the volatile composition 24 to the base material 12 and/or to the article 10 comprises combining the volatile composition 24 and the base material 12 and/or the article 10 in a container and applying a pressure above atmospheric pressure on the volatile composition 24 and base material 12 and/or the article 10. Pressure may be applied in a range from about 1 psi to about 40 psi, from about 5 psi to about 30 psi, or from about 10 psi to about 20 psi, at about 5 psi, at about 10 psi, at about 15 psi, at about 20 psi, at about 25 psi, at about 30 psi, at about 35 psi, at about 40 psi, and/or at pressures therein between. The pressure may be applied for a period of time from about 1 minute to about 10 hours, for about 30 minutes, for about 1 hour, for about 2 hours, for about 3 hours, for about 4 hours, for about 5 hours for about 6 hours, for about 7 hours, for about 8 hours, for about 9 hours, for about 10 hours, or longer if needed to apply sufficient amounts of the volatile composition 24 to the base material 12 and/or the article 10 to achieve a desired load of the volatile composition 24 to the base material 12 and/or the article 10 or release of the volatile composition 24 from the base material 12 and/or the article 10. Appropriate pressures and times for a particular embodiment can be determined by one skilled in the art based on the identities and characteristics of the particular volatile composition 24 and base material 12 and/or article 10.

In certain embodiments, a method for applying the volatile composition 24 comprises combining the volatile composition 24 and base material 12 and/or the article 10 in a container and applying a vacuum below atmospheric pressure to the volatile composition 24 and the base material 12 and/or the article 10. Vacuum may be applied in a range from 0.001 mm Hg to about 700 mm Hg, or from about 5 Kpa to about 35 kPa, from about 10 Kpa to about 25 kPa, from about 20 Kpa to about 30 kPa, from about 15 Kpa to about 25 kPa, from about 25 Kpa to about 30 kPa, at about 5 kPa, at about 6 kPa, at about 7 kPa, at about 8 kPa, at about 9 kPa, at about 10 kPa, at about 15 kPa, at about 16 kPa, at about 17 kPa, at about 18 kPa, at about 19 kPa, at about 20 kPa, at about 22 kPa, at about 24 kPa, at about 26 kPa, at about 28 kPa, at about 30 kPa, and vacuums therein between. The vacuum may be applied for a period of time from about 1 minute to about 10 hours, for about 30 minutes, for about 1 hour, for about 2 hours, for about 3 hours, for about 4 hours, for about 5 hours for about 6 hours, for about 7 hours, for about 8 hours, for about 9 hours, for about 10 hours, or longer if needed to apply sufficient amounts of the volatile composition 24 to the base material 12 and/or the article 10 to achieve a desired load of the volatile composition 24 to the base material 12 and/or the article 10 or release of the volatile composition 24 from the base material 12 and/or the article 10.

In yet other embodiments, the method may comprise pressure and vacuum steps. The volatile composition 24 and the base material 12 and/or the article 10 may be combined and undergo vacuum treatment and pressure treatment, in no particular order. For example, the volatile composition 24 and the base material 12 and/or the article 10 may be combined in a container in an air-tight apparatus and a vacuum of 20 mm Hg to 80 mm Hg may be applied for about 1 minute to 10 hours. Pressure treatment of 1 psi to 40 psi may be applied for about 1 minute to about 10 hours and the time and amount of vacuum or pressure treatment may vary and depend upon the amount of volatile composition 24 to be loaded in the base material 12 and/or the article 10, the type of base material 12 used, the intended use of the article 10, and other characteristics of the article 10.

In certain embodiments, the base material 12 and/or the article 10 may be pre-treated with colorants, followed by treatment with the modulating coating 14. Colorants may include natural and synthetic dyes, water-resistant dyes, oil-resistant dyes, and combinations of water- and oil-resistant dyes. Colorants may be selected based on the composition of the base material 12, and is well within the skill of those in the art. Suitable water-resistant colorants include oil soluble colorants and wax soluble colorants. Examples of oil soluble colorants include Pylakrome Dark Green and Pylakrome Red (Pylam Products Company, Tempe Ariz.). Suitable oil-resistant colorants include water soluble colorants. Examples of water soluble colorants include FD&C Blue No. 1 and Carmine (Sensient, St. Louis, Mo.). A Lake type dye may also be used. Examples of Lake dyes are Cartasol Blue KRL-NA LIQ and Cartasol Yellow KGL LIQ (Clariant Corporation, Charlotte, N.C.). Pigments may also be used in coloring the base material 12 and may be added during or after the manufacture of the base material 12. Such coloring or dying methods are known to those skilled in the art, and any suitable dyes, pigments, or colorants are contemplated by the present invention. Colorants may be used to affect the overall surface charge of the silica or other hygroscopic substance 28 to enhance the interaction with the coating.

EXAMPLES

Example 1. Method for Making Modulating Coating 14 Treatment Suspension

Modulating coating 14 with maltodextrin/silica ratio 50:50 at 30% total solids concentration was made by dissolving maltrodextrin solids in a silica suspension. A pre-weighed (15 kg) silica suspension (Snowtex®-O from Nissan Chemical America Corporation; Houston, Tex.) was transferred to a large mixing container. Snowtex®-O contains silica nanoparticles at 20% wt/wt solids in water. Water (2 kg) was added to the silica suspension to ensure the final total solids concentration was 30%. Maltodextrin (3 kg) (Maltrin QD M500 from Grain Processing Corporation; Muscatine, Iowa) was added slowly to the stirring suspension of silica. The treatment suspension of modulating coating 14 was allowed to stir until all of the solid maltodextrin dissolved.

Example 2. Application of Modulating Coating 14 onto Outer Layer Base Material 12

A treatment suspension of modulating coating 14 was made as described in Example 1. The base material 12 in this example was a paper rod with dimensions 13.97 cm (length) and 0.64 cm (diameter); the paper material is A50 offset book paper (Glatfelter, York, Pa.). The mass of base material 12 was recorded before the base material 12 was dipped into the treatment suspension. Base material 12 was submerged in the treatment suspension for 5 seconds. The base material 12 was removed from the treatment suspension and allowed to air dry overnight. The mass of the base material 12 coated with modulating coating 14 was recorded, and the amount of modulating coating 14 deposited onto the base material 12 was calculated by subtracting the post-treatment mass from the pre-treatment mass. As the results summarized in Table 1 below illustrate, the average add-on level of modulating coating 14 onto base material 12 is 1.9% when the application method is dipping of the dry base material 12.

TABLE 1

| Sample | Pre-mass (g) | Post-mass (g) | Add-on (g) | Add-on (%) |
|---|---|---|---|---|
| 1 | 2.867 | 2.920 | 0.053 | 1.8 |
| 2 | 2.841 | 2.897 | 0.056 | 2.0 |
| 3 | 2.869 | 2.922 | 0.053 | 1.8 |
| 4 | 2.868 | 2.925 | 0.057 | 2.0 |
| 5 | 2.875 | 2.934 | 0.059 | 2.1 |
| 6 | 2.875 | 2.924 | 0.049 | 1.7 |
| 7 | 2.818 | 2.874 | 0.056 | 2.0 |
| 8 | 2.900 | 2.956 | 0.056 | 1.9 |
| 9 | 2.817 | 2.867 | 0.050 | 1.8 |
| 10 | 2.872 | 2.934 | 0.062 | 2.2 |
| Average | 2.860 | 2.915 | 0.055 | 1.9 |

Example 3. Application of Modulating Coating 14 into Several Layers of Base Material 12

A treatment suspension of modulating coating 14 was made as described in Example 1 with the following change: the water (2 kg) was replaced with methanol (2 kg). The base material 12 in this example was a paper rod with dimensions 13.97 cm (length) and 0.64 cm (diameter); the paper material is A50 offset book paper (Glatfelter; York, Pa.). The change in surface tension of the treatment suspension with methanol allowed for better penetration of the treatment suspension into the base material 12. The mass of base material 12 was recorded before dipping into the treatment suspension. This method allowed for a higher add-on load. Base material 12 was submerged in the treatment suspension for 5 seconds; the submerge time may range between 1 second to 30 seconds. The base material 12 was removed from the treatment suspension and allowed to air dry overnight. The mass of the base material 12 coated with modulating coating 14 was recorded, and the amount of modulating coating 14 deposited onto the base material 12 was calculated by subtracting the post-treatment mass from the pre-treatment mass. As the results summarized in Table 2 below illustrate, the average add-on level of modulating coating 14 onto base material 12 is 3.7% when the treatment suspension contains methanol.

TABLE 2

| Sample (n = 3) | Pre-mass (g) | Post-mass (g) | Add-on (g) | Add-on (%) |
|---|---|---|---|---|
| Average | 2.856 | 2.961 | 0.105 | 3.7 |

Example 4. Application of Modulating Coating 14 by Vacuum-Driven Infusion for Higher Load Level A treatment suspension of modulating coating 14 was made as described in Example 1 and transferred to a container. The mass of base material 12 was recorded. The base material 12 was then submerged in the treatment suspension and placed under vacuum (25 mm Hg) for 5 minutes. The vacuum was removed, and the base material 12 was removed from the treatment suspension. The base material 12 treated with modulating coating 14 was placed under vacuum (25 mm Hg) for 1 minute to dry. Post-treatment mass was recorded, and the modulating coating 14 load level was calculated by subtracting the pre-mass from the post-mass. As the results summarized in Table 3 below illustrate, the average add-on level of modulating coating 14 onto base material 12 is 17.1% when the treatment suspension was infused via vacuum.

TABLE 3

| Sample | Pre-mass (g) | Post-mass (g) | Add-on (g) | Add-on (%) |
|---|---|---|---|---|
| 1 | 2.883 | 3.379 | 0.496 | 17.2 |
| 2 | 2.872 | 3.361 | 0.489 | 17.0 |
| 3 | 2.890 | 3.380 | 0.490 | 17.0 |
| Average | 2.882 | 3.373 | 0.492 | 17.1 |

Example 5. Weight-Loss Study 1

Base material 12 was loaded with fragrance Agilex 5224738 (Agilex Flavors & Fragrances; Piscataway, N.J.). The fragrance loaded test samples were allowed to sit at ambient conditions (temp. 21° C.-27° C.; relative humidity 40%-60%), and the mass of each was recorded at specified times. FIG. 5 is a graph showing the release rate in grams per day of the volatile composition, and FIG. 6 is a graph showing the cumulative amount of volatile composition released over time.

Example 6. Weight-Loss Study 2

Figure 7:
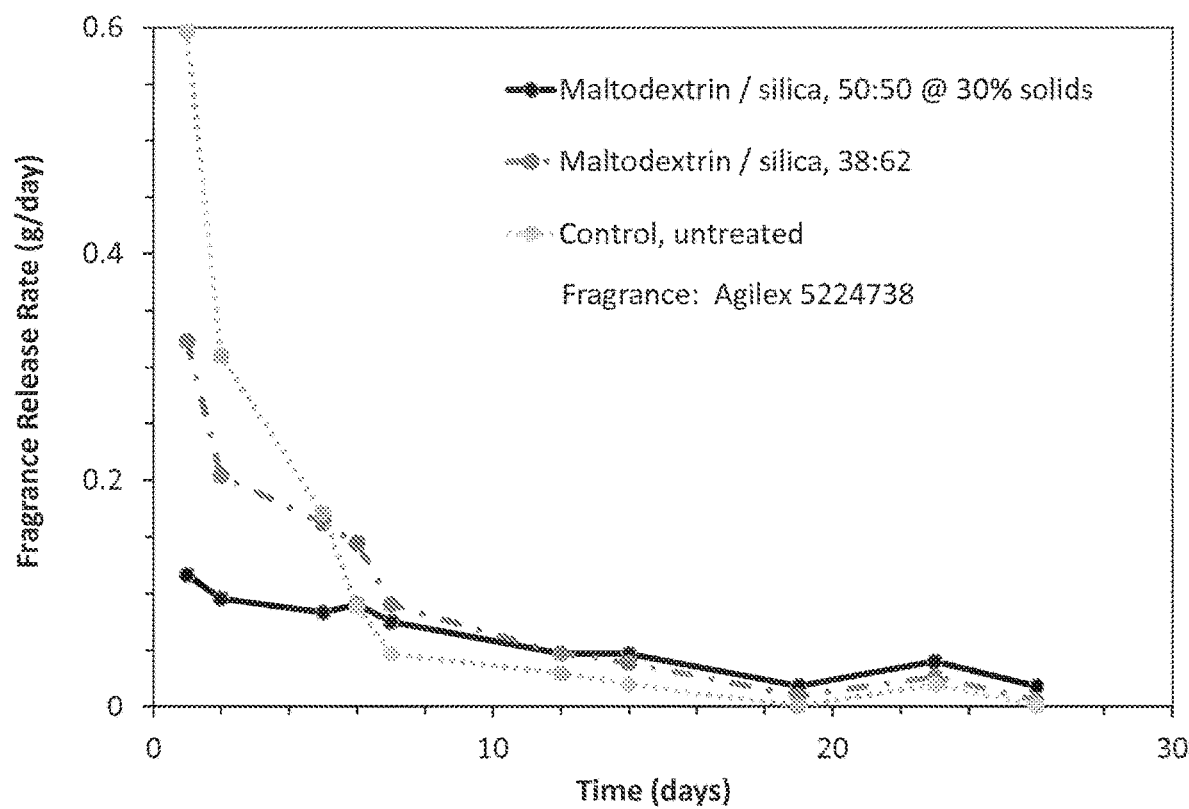
FIG. 7 is a graph showing the release rate in grams per day of a volatile composition loaded in an uncoated article and loaded in articles coated with modulating coatings using different ratios of barrier substances and hygroscopic substances.
Figure 8:
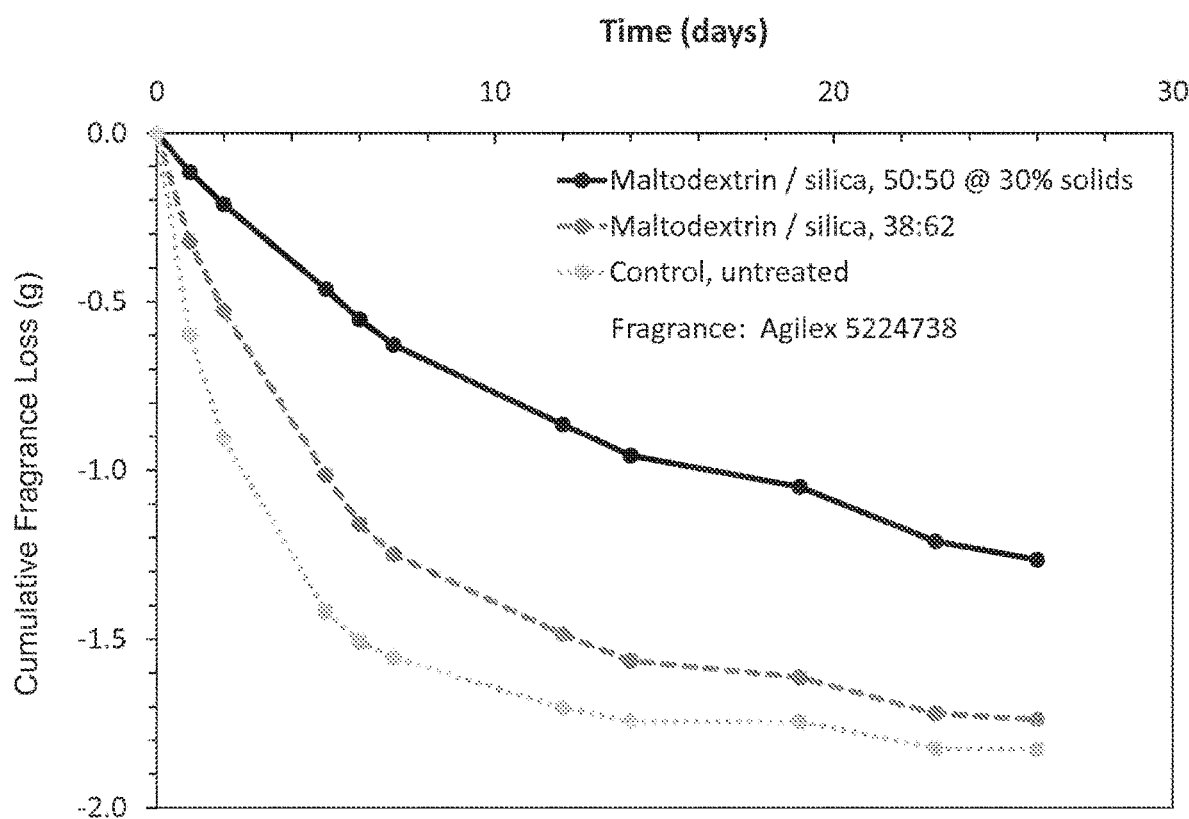
FIG. 8 is a graph showing the cumulative amount released over time of a volatile composition loaded in an uncoated article and loaded in articles coated with modulating coatings using different ratios of barrier substances and hygroscopic substances.

Base material 12 treated with modulating coating 14 exhibits a steady release of fragrance over time. Base material 12 treated with modulating coating 14, as described in Example 2, was loaded with fragrance Agilex 5224738 (Agilex Flavors & Fragrances; Piscataway, N.J.). A second set of samples of base material 12 treated with modulating coating 14 with maltodextrin/silica ratio 38:62 was loaded with fragrance Agilex 5224738. Base material 12 without modulating coating 14 was loaded with the same fragrance Agilex 5224738. The fragrance loaded test samples were allowed to sit at ambient conditions (temp. 21° C.-27° C.; relative humidity 40%-60%), and the mass of each was recorded at specified times. FIG. 7 is a graph showing the release rate in grams per day of the volatile composition from each sample, and FIG. 8 is a graph showing the cumulative amount of volatile composition released over time from each sample.

Example 7. Weight-Loss Study 3

FIG. 9 is a graph showing base material 12 treated with modulating coating 14 and loaded with a smaller amount of a fragrance composition having a higher concentration of volatile compounds provided a steady release of fragrance over time. Likewise, base material 12 treated with modulating coating 14 and loaded with a larger amount of a fragrance composition having a lower concentration of volatile compounds provided a substantially similar steady release of fragrance over time.

Sample A, base material 12 treated with modulating coating 14, as described in Example 2, was loaded with fragrance Arylessence AH179443 (Arylessence, Inc.; Marietta, Ga.). Sample B, base material 12 treated with modulating coating 14, was loaded with a lower concentration of fragrance Arylessence AH179443 (labeled "Arylessence LC"). Samples C and D, two sets of base material 12 without modulating coating 14 were loaded with the same two fragrances, respectively. The fragrance loaded test samples were allowed to sit at ambient conditions (temp. 21° C.-27° C.; relative humidity 40%-60%), and the mass of each was recorded at specified times. FIG. 9 is a graph showing the release rate in grams per day of the volatile composition from each sample, and FIG. 10 is a graph showing the cumulative amount of volatile composition released over time from each sample. As illustrated in Table 4, the amount of fragrance loaded onto base material 12 is affected when the modulating coating 14 is applied. (n=3)

TABLE 4

| Sample | Sample Description | Pre-mass (g) | Post-mass (g) | Amount Load (g) |
| --- | --- | --- | --- | --- |
| B | Maltrodextrin/silica, 50:50 @ 30% solids, Arylessence LC | 3.63 | 5.03 | 1.40 |
| D | Control, untreated, Arylessence LC | 3.54 | 5.94 | 2.40 |
| A | Maltrodextrin/silica, 50:50 @30% solids, Arylessence AH5224438 | 3.63 | 5.10 | 1.47 |
| C | Control, untreated, Arylessence AH5224438 | 3.54 | 5.75 | 2.21 |

Example 8. Weight-Loss Study 4

Figure 11:
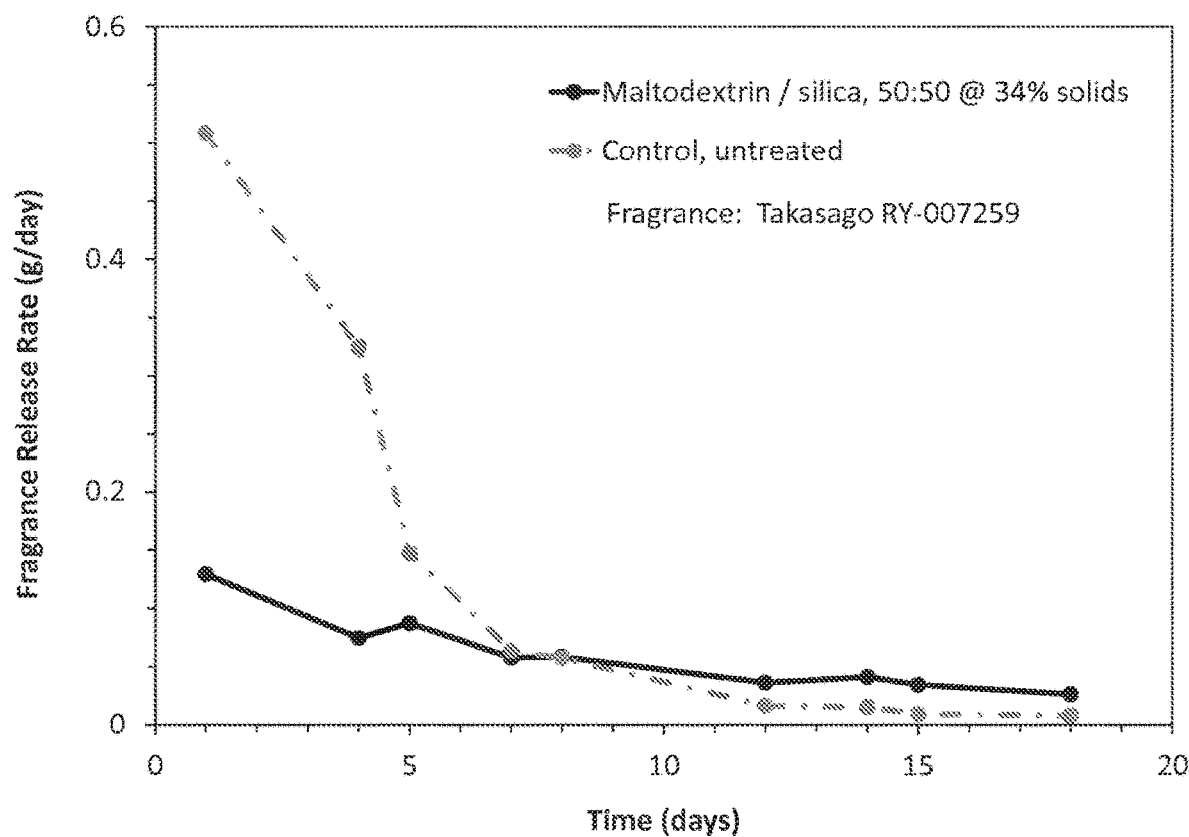
FIG. 11 is a graph showing the release rate in grams per day of a concentrated volatile composition loaded in an article coated with a modulating coating and loaded in an uncoated article.
Figure 12:
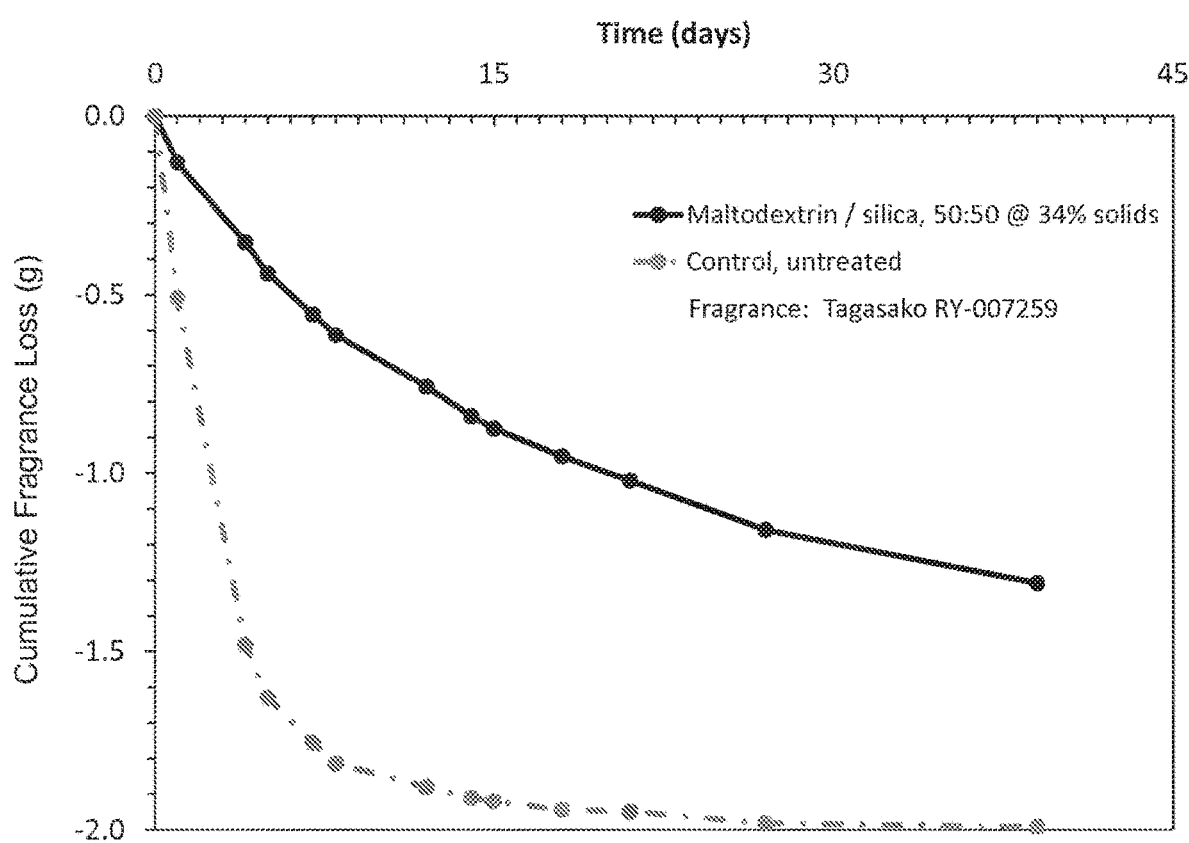
FIG. 12 is a graph showing the cumulative amount released over time of a concentrated volatile composition loaded in an article coated with a modulating coating and loaded in an uncoated article.

Modulating coating 14 allows for more fragrance release in the latter half of the material use-cycle. Base material 12 treated with modulating coating 14 exhibits a steady release of fragrance over time. Base material 12 treated with modulating coating 14 was loaded with fragrance Takasago RY-007259 (Takasago International Corporation; Rockleigh, N.J.). Base material 12 without modulating coating 14 was loaded with the same fragrance Takasago RY-007259. The fragrance loaded test samples were allowed to sit at ambient conditions (temp. 21° C.-27° C.; relative humidity 40%-60%), and the mass of each was recorded at specified times. FIG. 11 is a graph showing the release rate in grams per day of the volatile composition from each sample, and FIG. 12 is a graph showing the cumulative amount of volatile composition released over time from each sample.

Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications may be made without departing from the scope of the claims below.

That which is claimed is:

1. A method of manufacturing a fragrance-releasing article, the article comprising a base material having fibers and pores, the method comprising:
    applying a volatile composition to the base material;
    applying a modulating coating to at least one outer surface of the base material, the modulating coating comprising a hygroscopic substance and a barrier substance dispersed therein;
    wherein the hygroscopic substance comprises silica particles that are sized to attract water vapor without attracting liquid water;
    subjecting the combination of the base material, the modulating coating, and the volatile composition to a pressure that is different from atmospheric pressure;
    wherein the fragrance-releasing article exhibits a ratio of a first day weight-loss value to a last day weight-loss value in a range of 1 to 20 over a 30 day life cycle of the fragrance-releasing article.

2. The method of claim 1, wherein the barrier substance comprises a member selected from the group consisting of maltodextrins, dextrins, polysaccharides, carbohydrates, natural unmodified starches, modified starches, and combinations thereof.

3. The method of claim 1, wherein the volatile composition comprises a member selected from the group consisting of fragrances, flavor compounds, odor-eliminating compounds, aromatherapy compounds, natural oils, essential oils, water-based scents, odor neutralizing compounds, and combinations thereof.

4. The method of claim 1, wherein the barrier substance is grouped around particles of the hygroscopic substance through electrostatic interactions in the modulating coating due to a surface charge of the hygroscopic substance.

5. The method of claim 1, wherein the hygroscopic substance comprises particles with a diameter ranging from 1 nm to 100 nm.

6. The method of claim 1, wherein the barrier substance hinders a release of the volatile composition through the modulating coating; and wherein the hygroscopic substance facilitates the release of the volatile composition through the modulating coating due to presence of particles of the hygroscopic substance.

7. The method of claim 1, wherein subjecting the combination of the base material, the modulating coating, and the volatile composition to a pressure that is different from atmospheric pressure comprises subjecting the combination of the base material, the modulating coating, and the volatile composition to a pressure that is less than atmospheric pressure.

8. The method of claim 7, wherein the pressure is in a range from 0.001 mm Hg to 700 mm Hg.

9. The method of claim 1, wherein subjecting the combination of the base material, the modulating coating, and the volatile composition to a pressure that is different from atmospheric pressure comprises subjecting the combination of the base material, the modulating coating, and the volatile composition to a pressure that is greater than atmospheric pressure.

10. The method of claim 9, wherein the pressure is in a range from 1 psi to 40 psi.

11. The method of claim 1, wherein the pressure is applied for a period of up to 1 hour and the pressure is variable during the period.

12. The method of claim 1, wherein subjecting the combination of the base material, the modulating coating, and the volatile composition to a pressure that is different from atmospheric pressure comprises subjecting the combination of the base material, the modulating coating, and the volatile composition to a pressure that is less than atmospheric pressure, followed by a pressure that is greater than atmospheric pressure.

13. The method of claim 1, wherein particles of the hygroscopic substance attract water molecules from a surrounding atmosphere into the modulating coating to displace the volatile composition trapped by the barrier substance within the modulating coating.

14. The method of claim 5, wherein the barrier substance comprises maltodextrin.

15. The method of claim 14, wherein a weight ratio of the maltodextrin to the hygroscopic substance ranges from 99:1 to 1:99.

16. The method of claim 14, wherein a weight ratio of the maltodextrin to the hygroscopic substance ranges from 25:75 to 75:25.

17. The method of claim 14, wherein a weight ratio of the maltodextrin to the hygroscopic substance is approximately 50:50.

18. The method of claim 1, wherein at least some of the volatile composition is located within the modulating coating, wherein the modulating coating further comprises water that is absorbed or adsorbed to the hygroscopic substance.

19. A method of manufacturing a fragrance-releasing article, the article comprising a rod-shaped structural component comprising a base material wound around a vertical axis, the base material having fibers and pores, the method comprising:
    applying a volatile composition to the base material;
    applying a modulating coating to at least one outer surface of the base material, the modulating coating comprising a hygroscopic substance and a barrier substance dispersed therein;
    wherein the hygroscopic substance comprises silica particles that are sized to attract water vapor without attracting liquid water;
    subjecting the combination of the base material, the modulating coating, and the volatile composition to a pressure that is different from atmospheric pressure;
    wherein the fragrance-releasing article exhibits a ratio of a first day weight-loss value to a last day weight-loss value in a range of 1 to 20 over a 30 day life cycle of the fragrance-releasing article.

* * * * *